(12) United States Patent
Lynn et al.

(10) Patent No.: US 11,998,676 B2
(45) Date of Patent: Jun. 4, 2024

(54) METHODS AND SYSTEMS OF VARIABLE ASPIRATION CONTROL IN SURGICAL PROCEDURES

(71) Applicants: SMITH & NEPHEW, INC., Memphis, TN (US); SMITH & NEPHEW ORTHOPAEDICS AG, Zug (CH)

(72) Inventors: Christopher J. Lynn, Austin, TX (US); Johnson E. Goode, Austin, TX (US)

(73) Assignees: SMITH & NEPHEW, INC., Memphis, TN (US); SMITH & NEPHEW ORTHOPAEDICS AG, Zug (CH)

( * ) Notice: Subject to any disclaimer, the term of this patent is extended or adjusted under 35 U.S.C. 154(b) by 0 days.

(21) Appl. No.: 18/247,323

(22) PCT Filed: Oct. 26, 2021

(86) PCT No.: PCT/US2021/056543
§ 371 (c)(1),
(2) Date: Mar. 30, 2023

(87) PCT Pub. No.: WO2022/093740
PCT Pub. Date: May 5, 2022

(65) Prior Publication Data
US 2023/0381398 A1    Nov. 30, 2023

Related U.S. Application Data

(60) Provisional application No. 63/105,635, filed on Oct. 26, 2020.

(51) Int. Cl.
*A61B 18/14*    (2006.01)
*A61B 17/32*    (2006.01)
(Continued)

(52) U.S. Cl.
CPC .......... *A61M 1/75* (2021.05); *A61B 17/3205* (2013.01); *A61B 18/14* (2013.01); *A61B 18/148* (2013.01);
(Continued)

(58) Field of Classification Search
CPC ....... A61M 1/75; A61M 1/76; A61B 17/3205; A61B 18/14; A61B 18/148;
(Continued)

(56) References Cited

U.S. PATENT DOCUMENTS

2003/0163126 A1    8/2003  West, Jr.
2008/0188848 A1    8/2008  Deutmeyer et al.
(Continued)

FOREIGN PATENT DOCUMENTS

WO    2018170063 A1    9/2018
WO    2020172659 A1    8/2020

OTHER PUBLICATIONS

International Search Report and Written Opinion for International Application No. PCT/US2021/056543, International Filing Date Oct. 26, 2021, dated Feb. 25, 2022.

*Primary Examiner* — Sean W Collins
(74) *Attorney, Agent, or Firm* — Dickinson Wright PLLC; Mark E. Scott

(57) ABSTRACT

Variable aspiration control in surgical procedures. At least one example is a method of performing a surgical procedure, the method comprising: driving, by a surgical controller, a motor within a handpiece coupled to a resection instrument, the driving causes mechanical resection of tissue by the resection instrument; aspirating, by a peristaltic pump associated with the surgical controller, fluid and tissue fragments through a suction lumen of the resection instrument during the resection of tissue; and modulating, by the surgical controller, speed of the peristaltic pump during the driving (Continued)

and aspirating, the modulating responsive to an interface device defined on an exterior surface of the handpiece.

11 Claims, 10 Drawing Sheets

(51) Int. Cl.
    *A61B 17/3205*     (2006.01)
    *A61M 1/00*     (2006.01)
    *A61B 17/00*     (2006.01)
    *A61B 18/00*     (2006.01)

(52) U.S. Cl.
    CPC ..... *A61M 1/76* (2021.05); *A61B 2017/00973* (2013.01); *A61B 2017/320064* (2013.01); *A61B 2018/00208* (2013.01); *A61B 2018/00577* (2013.01); *A61B 2018/00708* (2013.01); *A61B 2018/00744* (2013.01); *A61B 2217/005* (2013.01); *A61B 2218/007* (2013.01)

(58) Field of Classification Search
    CPC ........... A61B 2018/00208; A61B 2018/00577; A61B 2018/00708; A61B 2018/00744; A61B 2217/005; A61B 2218/007
    See application file for complete search history.

(56) References Cited

U.S. PATENT DOCUMENTS

| | | | |
|---|---|---|---|
| 2013/0079702 A1* | 3/2013 | Klein | A61M 3/0208 604/22 |
| 2013/0267779 A1* | 10/2013 | Woolford | A61B 17/34 600/156 |
| 2015/0173827 A1 | 6/2015 | Bloom et al. | |
| 2020/0163708 A1 | 5/2020 | Woloszko et al. | |
| 2020/0323582 A1 | 10/2020 | Willhite et al. | |
| 2022/0160419 A1* | 5/2022 | Hoegstrom | A61B 18/148 |

* cited by examiner

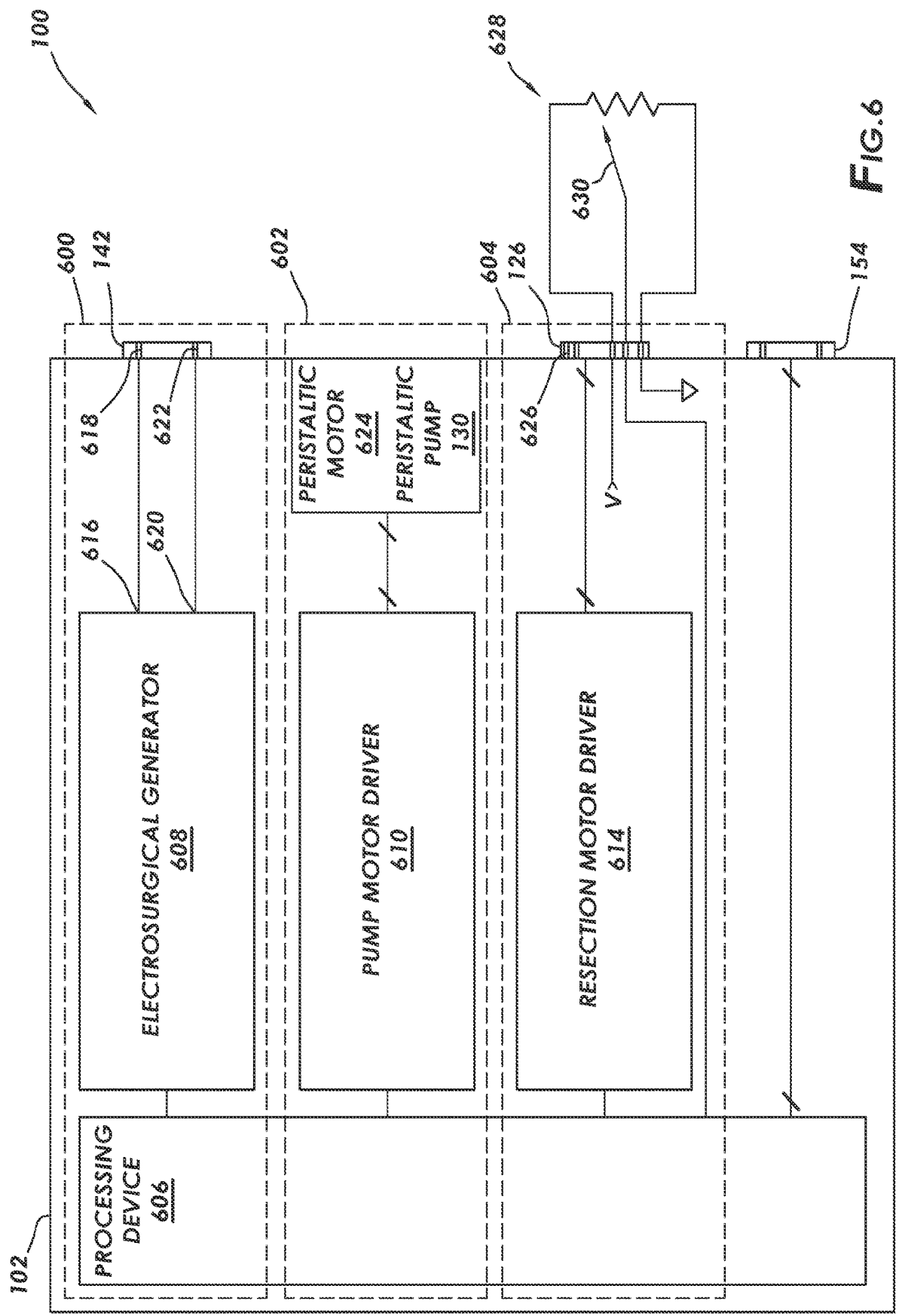

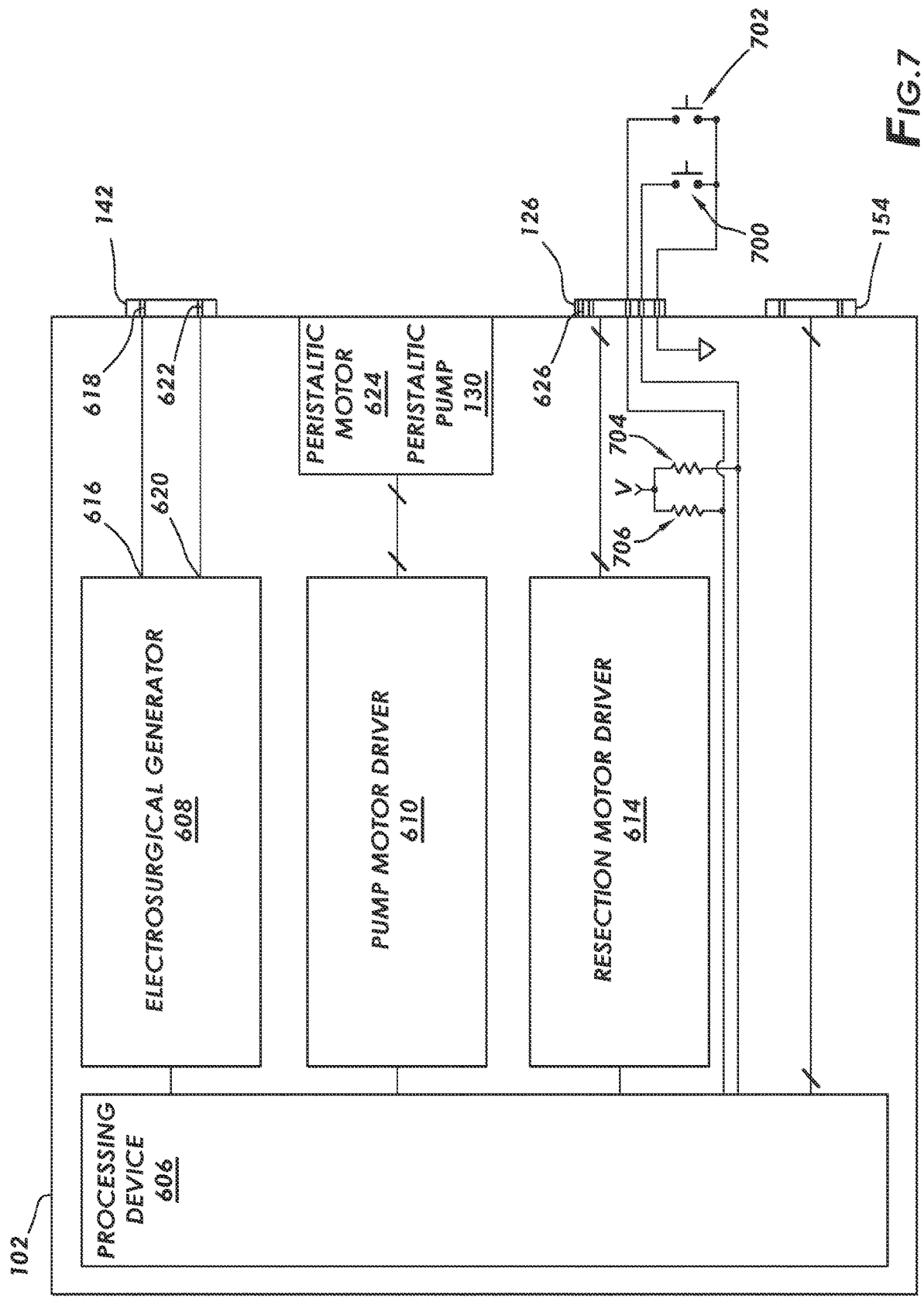

METHODS AND SYSTEMS OF VARIABLE ASPIRATION CONTROL IN SURGICAL PROCEDURES

CROSS-REFERENCE TO RELATED APPLICATIONS

This application is a U.S. National Phase of entry of PCT Application No. PCT/US2021/056543 filed Oct. 26, 2021 titled "Methods and Systems of Variable Aspiration Control in Surgical Procedures." The PCT application claims the benefit of U.S. provisional application Ser. No. 63/105,635 filed Oct. 26, 2020 and titled "Arthroscopic Resection Probe with Variable Aspiration Control." Both the PCT and the provisional application are incorporated by reference herein as if reproduced in full below.

BACKGROUND

Related-art mechanical resection handpieces comprise a valve within the flow path between the resection device and the source of suction, such as wall suction in a surgical room. During mechanical resection procedures, the surgeon adjusts the flow rate along the flow path within the resection device by adjusting the valve position. When higher flow rates are desired, the surgeon opens the valve more, and when lower flow rates are desired, the surgeon closes the valve more. By contrast, in related-art electrosurgical ablation procedures (e.g., plasma-based ablation), the control of the flow rate is performed automatically by the ablation controller responsive to one or more electrical parameters associated with the ablation, such as impedance of the electrical pathway or energy provided to the active electrode for the ablation procedure.

SUMMARY

A first example is a method of performing a surgical procedure, the method comprising: driving, by a surgical controller, a motor within a handpiece coupled to a resection instrument, the driving causes mechanical resection of tissue by the resection instrument; aspirating, by a peristaltic pump associated with the surgical controller, fluid and tissue fragments through a suction lumen of the resection instrument during the mechanical resection of tissue; and modulating, by the surgical controller, speed of the peristaltic pump during the driving and aspirating, the modulating responsive to an interface device defined on an exterior surface of the handpiece.

In the example first method, handpiece may not include a valve in an aspiration pathway through the handpiece.

In the example first method, modulating speed of the peristaltic pump may further comprise: reading the interface device being a positional-interface device defined on the handpiece, the reading results in a position; and setting speed of the peristaltic pump based directly on the position.

In the example first method, modulating speed of the peristaltic pump may further comprise: receiving an indication of actuation of the interface device being an up button defined on the handpiece; and increasing speed of the peristaltic pump based on the indication of actuation of the up button. Modulating speed of the peristaltic pump may further comprise: receiving an indication of actuation of the interface device being a down button defined on the handpiece; and decreasing speed of the peristaltic pump based on the indication of actuation of the down button. The up button and the down button may be at least one selected from a group consisting of: separate and distinct buttons; respective positions of a rocker switch; and respective positions of a momentary rocker switch.

The example first method may further comprise: stopping, by the surgical controller, the motor of the handpiece at a rotational position such that a cutting window defined by the resection instrument is at least partially blocked; and then providing, by the surgical controller, electrical energy to an active electrode defined on a distal end of the resection instrument, the electrical energy causes ablation of tissue proximate to the active electrode. The example first method may also further comprise modulating, by the surgical controller, speed of the peristaltic pump during the ablation of tissue, the modulating responsive to the interface device. The example first method may also further comprise: ceasing the providing electrical energy to the active electrode; and then driving, by the surgical controller, the motor within the handpiece, the driving again causes mechanical resection of tissue by the resection instrument; and aspirating, by the peristaltic pump, fluid and tissue fragments through the suction lumen at a pump speed selected based on at least one selected from a group comprising: a pump speed of an immediately previous mechanical resection of tissue; a default pump speed for mechanical resection of tissue.

A second example method is a method of performing a surgical procedure, the method comprising: providing, by a surgical controller, electrical energy to an active electrode defined on a distal end of a resection tool, the electrical energy causes ablation of tissue proximate to the active electrode; drawing, by a peristaltic pump associated with the surgical controller, fluid and tissue fragments through a suction lumen of the resection tool during the ablation of tissue; and modulating, by the surgical controller, speed of the peristaltic pump during the providing and the drawing, the modulating responsive to an interface device defined on an exterior surface of the resection tool.

In the example second method, modulating the speed of the peristaltic pump may further comprise: reading position of the interface device being a positional-interface device defined on the resection tool, the reading results in a position; and setting the speed of the peristaltic pump based on the position. Modulating the speed of the peristaltic pump may further comprise: receiving an indication of up actuation of the interface device being an up button defined on the resection tool; and increasing, based on the indication of up actuation, the speed of the peristaltic pump. Modulating the speed of the peristaltic pump may further comprise: receiving an indication of down actuation of the interface device in the form of a down button defined on the resection tool; and decreasing, based on the indication of down actuation, the speed of the peristaltic pump.

The example second method may further comprise: receiving, by the surgical controller, an indication of a selected mode of operation from a plurality of modes of operation, each mode of operation defines a range of pump speeds, and each range of pump speeds less than an entire range of pump speed of the peristaltic pump; and wherein modulating the speed of the peristaltic pump comprises setting a speed of the peristaltic pump within the range of pump speeds defined by the selected mode of operation, and the modulation responsive to the interface device. Setting the speed of the peristaltic pump may further comprise: reading position of the interface device being a positional-interface device defined on the resection tool, the reading results in a position; and setting the speed of the peristaltic pump based on the position. Setting the speed of the peristaltic pump may further comprise: receiving an indication of up actuation of the interface device being an up button defined on the resection tool; and increasing, based on the indication of up actuation, the speed of the peristaltic pump within the range of pump speeds of the selected mode of operation. Setting the speed of the peristaltic pump may further comprise: receiving an indication of down actuation of the interface device in the form of a down button defined on the resection tool; and decreasing, based on the indication of down actuation, the speed of the peristaltic pump within the range of pump speeds of the selected mode of operation.

The example second method may further comprise: ceasing the providing electrical energy to the active electrode; and then driving, by the surgical controller, a motor within the resection tool, the driving causes mechanical resection of tissue by the resection instrument; and aspirating, by the peristaltic pump associated with the surgical controller, fluid and tissue fragments through the suction lumen of the resection instrument during the mechanical resection of tissue; and modulating, by the surgical controller, speed of the peristaltic pump during the driving and aspirating, the modulating based on the interface device.

Another example is a first surgical system comprising: a resection controller coupled to a motor in handpiece, and the handpiece coupled to a resection instrument defining a cutting element, and the handpiece comprises an interface device defined on an exterior surface of the handpiece; and a peristaltic pump controller coupled to a motor of a peristaltic pump, the peristaltic pump coupled to a suction lumen of the resection instrument. The surgical system may be configured to: drive the motor within a handpiece to cause mechanical resection of tissue by the resection instrument; aspirate fluid and tissue fragments through the suction lumen of the resection instrument during the mechanical resection of tissue; and modulate speed of the peristaltic pump during the driving and aspirating, the modulation responsive to the interface device.

In the example first surgical system, the handpiece may not include a valve in an aspiration pathway through the handpiece.

In the example first surgical system, when the surgical system modulates speed of the peristaltic pump, the surgical system may be further configured to: read the interface device being a positional-interface device defined on the handpiece, the reading results in a position; and set speed of the peristaltic pump based on the position.

In the example first surgical system, when the surgical system modulates speed of the peristaltic pump, the surgical system may be further configured to: receive an indication of actuation of the interface device being an up button defined on the handpiece; and increase speed of the peristaltic pump based on the indication of actuation of the up button. When the surgical system modulates speed of the peristaltic pump, the surgical system may be further configured to: receive an indication of actuation of the interface device being a down button defined on the handpiece; and decrease speed of the peristaltic pump based on the indication of actuation of the down button. The up button and the down button may be at least one selected from a group consisting of: separate and distinct buttons; respective positions of a rocker switch; and respective positions of a momentary rocker switch.

The example first surgical system may further comprise an electrosurgical controller coupled to an active electrode of defined on the resection instrument. And the surgical system may be further configured to: stop the motor of the handpiece at a rotational position such that the cutting element blocks a cutting window defined by the resection instrument; and then provide electrical energy to the active electrode to cause ablation of tissue proximate to the active electrode. The surgical system may be further configured to modulate speed of the peristaltic pump during the ablation of tissue, the modulation responsive to the interface device. The surgical system may be further configured to: cease the providing of electrical energy to the active electrode; and then drive the motor within the handpiece, the driving again causes mechanical resection of tissue by the resection instrument; and aspirate fluid and tissue fragments through the suction lumen at a pump speed selected based on at least one selected from a group comprising: a pump speed of an immediately previous mechanical resection; a default pump speed for mechanical resection of tissue.

Another example is a second surgical system comprising: an electrosurgical controller coupled to an active electrode disposed on a distal end of a resection tool; and a peristaltic pump controller comprising motor and a peristaltic pump, the peristaltic pump coupled to a suction lumen of the resection tool. The surgical system may be configured to: provide electrical energy to the active electrode to cause ablation of tissue proximate to the active electrode; draw fluid and tissue fragments through the suction lumen the ablation of tissue; and modulate speed of the peristaltic pump during the providing and the drawing, the modulation responsive to an interface device defined on an exterior surface of the resection tool.

In the example second surgical system, when the surgical system modulates the speed of the peristaltic pump, the surgical system may be further configured to: read position of the interface device being a positional-interface device defined on the resection tool, the reading results in a position; and set the speed of the peristaltic pump based on the position.

In the example second surgical system, when the surgical system modulates the speed of the peristaltic pump, the surgical system may be further configured to: receive an indication of up actuation of the interface device being an up button defined on the resection tool; and increase, based on the indication of up actuation, the speed of the peristaltic pump. The example second surgical system may be further configured to: receive an indication of down actuation of the interface device in the form of a down button defined on the resection tool; and decrease, based on the indication of down actuation, the speed of the peristaltic.

The example second surgical system may be further configured to: receive an indication of a selected mode of operation from a plurality of modes of operation, each mode of operation defines range of pump speeds, and each range of pump speeds less than an entire range of pump speed of the peristaltic pump; and modulate speed by setting a speed of the peristaltic pump within the range of pump speeds of the selected mode of operation, and the modulation based on the interface device. When the surgical system sets the speed of the peristaltic pump, the surgical system may be further configured to: read position of the interface device being a positional-interface device defined on the resection tool, the reading results in a position; and set the speed of the peristaltic pump within the range of pump speeds of the selected mode of operation based on the position. When the surgical system sets the speed of the peristaltic pump, the surgical system may be further configured to: receive an indication of up actuation of the interface device being an up button defined on the resection tool; and increase the speed of the peristaltic pump within the range of pump speeds of the selected mode of operation. When the surgical system sets the speed of the peristaltic pump, the surgical system may be further configured to: receive an indication of down actuation of the interface device being a down button defined on the resection tool; and decrease the speed of the peristaltic pump within the range of pump speeds of the selected mode of operation.

The example second surgical system may further comprise a resection controller coupled to a motor in a handpiece of the resection tool, and the handpiece coupled to a cutting element defined by a resection instrument of the resection tool, the resection instrument coupled to the handpiece. And the surgical system may be further configured to: cease the providing of electrical energy to the active electrode; and then drive the motor within the handpiece, the driving causes mechanical resection of tissue by the resection instrument; and aspirate fluid and tissue fragments through the suction lumen of the resection instrument during the mechanical resection of tissue; and modulate speed of the peristaltic pump during the driving and aspirating, the modulation based on the interface device.

Yet another example is a surgical controller comprising: a resection motor driver coupled to motor terminals in a connector of the surgical controller, the resection motor driver configured to drive a motor in a handpiece; an electrosurgical generator coupled to terminals in a connector of the surgical controller; a pump motor driver coupled to a motor of a peristaltic pump, a rotor of the peristaltic pump accessible on an external surface of the surgical controller; and a processing device coupled to the resection motor driver, the electrosurgical generator, the pump motor driver, and interface terminals in a connector of the surgical controller. The processing device may be configured to: command the resection motor driver to drive the motor in the handpiece to cause resection of tissue; command the electrosurgical generator to provide electrical energy to an active electrode to cause ablation of tissue proximate to the active electrode; read a value indicative of actuation of an interface device by way of the interface terminals; and modulate a speed setpoint provided to the pump motor driver responsive to the value indicative of actuation.

In the example surgical controller, the processing device may be further configured to: receive an indication of a mode of operation from a plurality of modes of operation, each mode of operation defines range of pump speeds, and each range of pump speeds less than an entire range of pump speed of the peristaltic pump; and wherein when the processing system modulates the speed setpoint, the processing system is further configured to modulate the speed setpoint within the range of pump speeds defined by mode of operation.

BRIEF DESCRIPTION OF THE DRAWINGS

For a detailed description of example embodiments, reference will now be made to the accompanying drawings in which:

FIG. 6 shows a block diagram of a surgical system in accordance with at least some embodiments;

FIG. 7 shows a block diagram of a surgical system in accordance with at least some embodiments;

DEFINITIONS

Figure 1:
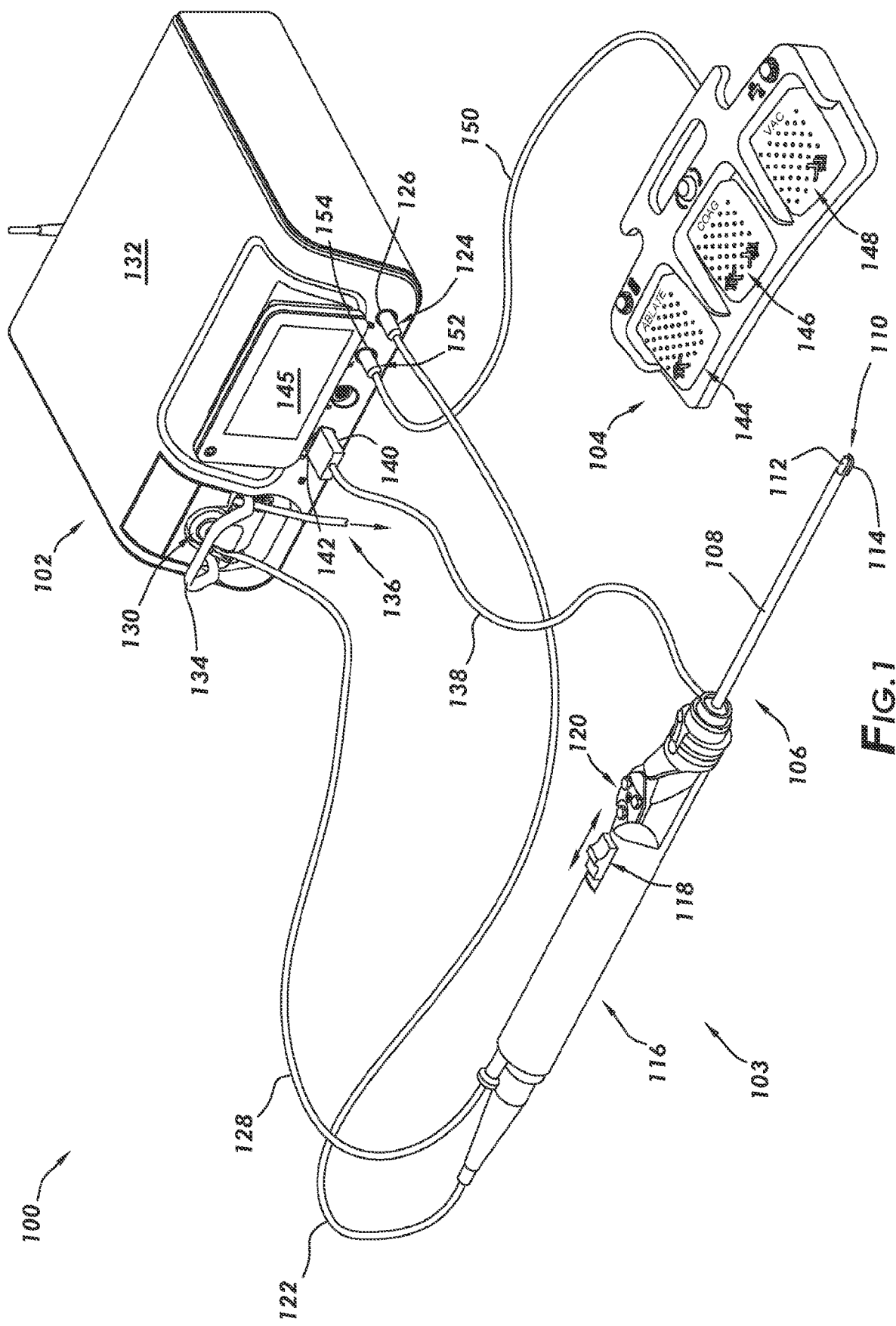
FIG. 1 shows a surgical system in accordance with at least some embodiments.

Various terms are used to refer to particular system components. Different companies may refer to a component by different names—this document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect connection via other devices and connections.

"Positional-interface device" shall mean an interface device whose position or orientation indicates a setpoint speed of a peristaltic pump. For example, the positional-interface device may be a slider whose position along a longitudinal axis of a handpiece indicates the setpoint speed, or a knob comprising a visual indication of the relative rotational position of the knob and thus the setpoint speed.

"Non-positional-interface device" shall mean an interface device whose implied setpoint speed of the peristaltic pump cannot be determined from the visual appearance of the device. For example, a capacitive touch sensor, a Boolean interaction device (e.g., up button and down button, momentary rocker switch), and knobs devoid of position indications, are non-limiting examples of non-positional-interface devices.

"Processing device" shall mean, alone or in combination, individual circuit components, an application specific integrated circuit (ASIC), a microcontroller with controlling software, a reduced-instruction-set computing (RISC) with controlling software, a digital signal processor (DSP), a processor with controlling software, a programmable logic device (PLD), or a field programmable gate array (FPGA), configured to read inputs and drive outputs responsive to the inputs.

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Various examples are directed to variable aspiration control in surgical procedures. More particularly, in the case of mechanical resection, examples are directed to enabling a surgeon to directly control speed of a peristaltic pump providing the aspiration flow by the surgeon's interaction with an interface device defined on the exterior surface of the handpiece. More particularly still, in various examples a surgical controller is communicatively coupled to the interface device and sets speed of the peristaltic pump based directly on the surgeon's interaction with the interface device. In the case of electrosurgical ablation, various examples are directed to enabling a surgeon to control speed of the peristaltic pump using the interface device. In one case, the surgeon controls the speed of the peristaltic pump over an entire range of speeds of the peristaltic pump using the interface device. In other cases, the surgeon controls the speed of the peristaltic pump within a predefined range of speeds, less than the entire range of speeds, the predefined range of speeds based on a selected mode of operation of the ablation. The specification first turns to an example system to orient the reader.

FIG. 1 shows a surgical system (not to scale) in accordance with at least some embodiments. In particular, the surgical system 100 comprises a surgical controller 102, a resection tool 103, and a foot pedal assembly 104. The resection tool 103 includes a resection instrument 106 that comprises an elongate shaft 108 defining a distal end 110. The example resection instrument 106 defines a cutting window 112 within which mechanical resection of tissue takes place. That is, the example resection instrument 106 defines an internal tube (not visible) telescoped within the elongate shaft 108. The internal tube also defines a cutting window of similar shape to the cutting window 112 defined by the elongate shaft 108. The internal tube is turned while the elongate shaft 108 remains stationary, and tissue that is drawn into the cutting windows is cut by the interaction of cutting elements defined by the elongate shaft 108 and internal tube. The example resection instrument 106 further defines an active electrode 114 disposed at the distal end 110 of the elongate shaft 108, the active electrode at a radial position opposite the cutting window 112. Thus, in the example system the resection tool 103 may be used for both mechanical resection and electrically-based ablation (e.g., plasma-based ablation) of tissue.

The example resection tool 103 further comprises a motor drive unit (MDU) or handpiece 116. Though not visible in FIG. 1, the handpiece 116 comprises a motor (e.g., electrical motor) disposed within the outer cover, and when the resection instrument 106 is coupled to the handpiece 116 the rotor of the motor is coupled to the internal tube to cause rotation of the internal tube relative to the stationary elongate shaft 108. The example handpiece 116 further defines an interface device illustratively shown a positional-interface device 118 defined on an exterior surface of the handpiece 116. During use, and as discussed in greater detail below, the surgeon may use the example positional-interface device 118 to set or select an aspiration flow rate through a suction lumen of the resection instrument 106 (e.g., through the internal diameters of the elongate shaft 108 and the internal tube disposed therein). For the example positional-interface device 118, the interaction may involve moving the positional-interface device 118 toward the distal end 110 to increase aspiration flow rate or moving the positional-interface device 118 away from the distal end 110 to decease aspiration flow rate. Other example interface devices are shown and discussed below. The handpiece 116 further defines additional buttons on the upper surface, such as buttons 120. The surgeon may interact with buttons 120 to set or select various operational parameters. In the context of mechanical resection, the surgeon may interact with buttons 120 to select the speed of the internal tube and/or the direction the internal tube turns with respect to the stationary elongate shaft 108 (e.g., clockwise, counter-clockwise, oscillate). In the context ablation, the surgeon may interact with the buttons 120 set a mode of operation of the ablation (e.g., high, medium, or low) or to toggle between an ablation mode and a non-ablative coagulation mode.

The resection tool 103 further comprises a flexible multi-conductor cable 122 housing one or more electrical leads (not specifically shown in FIG. 1), and the flexible multi-conductor cable 122 terminates in a wand connector 124. The wand connector 124 is mechanically and electrically coupled to the surgical controller 102 by way of a connector 126 defined on an outer surface (e.g., the front surface) of the enclosure 132 of the surgical controller 102. By way of the flexible multi-conductor cable 122, the surgical controller 102 may control the speed and direction of the motor within handpiece 116, read or receive signals and/or values indicative of the surgeon's interaction with the example positional-interface device 118, and/or read or receive signal indicative of the surgeon's interaction with the buttons 120.

Though not visible in the view of FIG. 1, the example resection tool 103 has one or more internal aspiration channels or fluid passageways. The fluid passageway of the resection tool 103 couples to a hose or flexible tubular member 128 used to provide suction or aspiration at the distal end 110 of the resection tool 103. In the example system, the flexible tubular member 128 is coupled to a peristaltic pump 130 illustratively shown as an integral component with the surgical controller 102 (i.e., residing at least partially within the enclosure 132 of the surgical controller 102). In other embodiments, an enclosure for the peristaltic pump 130 may be separate and distinct from the enclosure 132 for the surgical controller 102, but in any event the peristaltic pump 130 is operatively coupled to the surgical controller 102.

The peristaltic pump 130 comprises a rotor portion (not visible) and a stator portion (not visible). The flexible tubular member 128 is coupled within the peristaltic pump 130 by opening the cover of the peristaltic pump 130 using handle 134, and placing the flexible tubular member 128 between the rotor and stator. Movement of the rotor against the flexible tubular member 128 causes fluid movement toward the discharge 136. In the various examples, the peristaltic pump 130 creates a volume-controlled aspiration from a cavity or surgical field at the distal end 110 of the resection tool 103 (the surgical field not specifically shown), with the outflow rate based on speed of the peristaltic pump 130.

The resection tool 103, and specifically the resection instrument 106, further defines another flexible multi-conductor cable 138 housing one or more electrical leads (not specifically shown in FIG. 1). The multi-conductor cable 138 terminates in an ablation connector 140. The ablation connector 140 is mechanically and electrically coupled to the surgical controller 102 by way of a connector 142 defined on the outer surface (e.g., the front surface) of the enclosure 132 of the surgical controller 102. By way of the multi-conductor cable 138, the surgical controller 102 may provide electrical energy to the active electrode 114 for electrically-based ablation and/or coagulation. Moreover, the multi-conductor cable 138 may provide an electrical return path for the electrical circuit (e.g., the elongate shaft 108 may act as the return electrode for electrically-based procedures).

Still referring to FIG. 1, a display device or interface device 145 is visible through the enclosure 132 of the surgical controller 102, and in some cases a surgeon may select operational modes of the surgical controller 102 by way of the interface device 145. For example, by interacting with the interface device 145 in the form of a touch screen the surgeon may select a rotational mode for mechanical resection. As another example, using the interface device 145 in the form of a touch screen the surgeon may select an aggressiveness during ablation, such as a selecting a mode of operation of the ablation (e.g., high, medium, low). Further still, the surgical controller 102 may provide information to the surgeon by way of the interface device 145, such as an indication of the current mode of operation or a cumulative use time of the active electrode 114 for electrically-based ablation.

The example surgical system 100 also comprises the foot pedal assembly 104. The example foot pedal assembly 104 comprises three foot pedal devices 144, 146, and 148. In example cases, the surgeon may switch between mechanical resection and ablation based on interaction with the foot pedal assembly 104. During an example mechanical resection, the surgeon may select a direction of rotational and/or operational mode (e.g., rotate a first direction by pressing foot pedal device 144, and rotate the opposite direction by pressing foot pedal device 148). During an example ablation, the surgeon may selectively activate and deactivate the ablation (e.g., by interaction with the foot pedal device 144), and switch from ablation to coagulation (e.g., by interaction with the foot pedal device 146). In the example, the foot pedal assembly 104 is coupled to the surgical controller 102 by way of flexible multi-conductor cable 150 housing one or more electrical leads (not specifically shown in FIG. 1). The multi-conductor cable 150 terminates in a pedal connector 152. The pedal connector 152 is mechanically and electrically coupled to the surgical controller 102 by way of a connector 154 defined on the outer surface (e.g., the front surface) of the enclosure 132.

Figure 2:
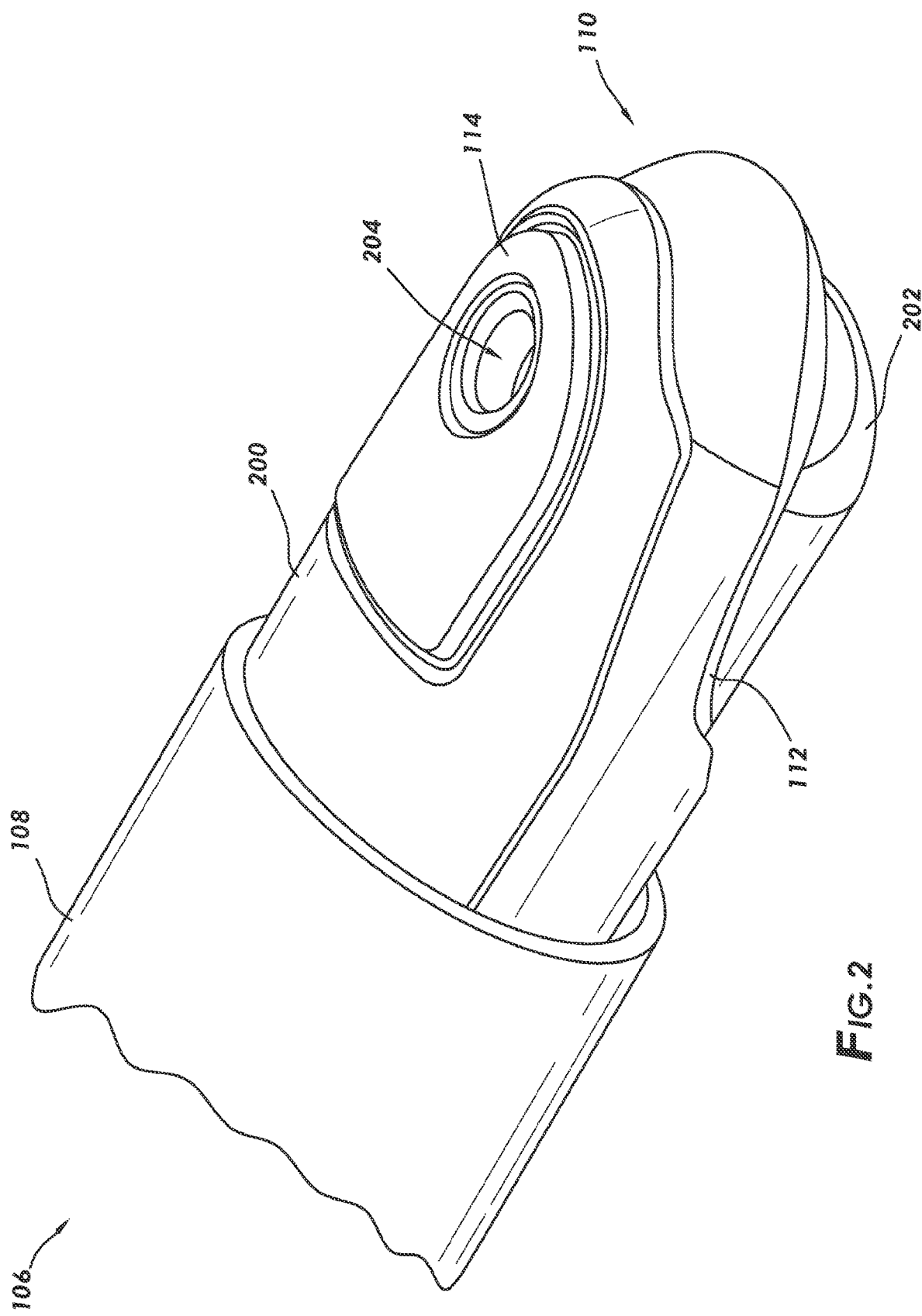
FIG. 2 shows a perspective view of a distal end of an example resection instrument in accordance with at least some embodiments.

FIG. 2 shows a perspective view of the distal end 110 of the example resection instrument 106. In the view of FIG. 2, the resection instrument 106 is rotated 180 rotational degrees about the longitudinal central axis in comparison to the view of FIG. 1 such that the active electrode 114 is on top in the view, and the cutting window 112 is facing down. In particular, visible in FIG. 2 is a portion of the cutting window 112, the active electrode 114, and a portion of the elongate shaft 108. Also visible in FIG. 2 is an insulator 200 (e.g., ceramic) that electrically isolates the active electrode 114 from the elongate shaft 108 used as a return electrode during ablation and coagulation. Moreover, FIG. 2 shows the internal tube 202, and in the configuration shown the internal tube 202 is stopped at a rotational position that at least partially blocks the cutting window 112. Stated otherwise, the corresponding cutting window defined by the internal tube 202 is within the internal diameter of the elongate shaft 108 at a rotational position that is misaligned with the cutting window 112.

The example active electrode 114 is disposed at the distal end 110. The active electrode 114 is a metallic material, and during ablation a plasma may form around and/or near the active electrode 114. The example active electrode 114 defines an aperture 204 that is fluidly coupled to a suction lumen defined within the internal diameter of the internal tube 202; however, in the view of FIG. 2 the suction lumen is not visible. During ablation the peristaltic pump 130 (FIG. 1) draws fluid and tissue products through the aperture 204 and along the suction lumen. More particularly, in example cases the surgical controller 102 (FIG. 1) is designed and constructed such that each time mechanical resection is stopped (e.g., releasing one of the foot pedal devices of the foot pedal assembly 104 (FIG. 1)), the surgical controller 102 stops the internal tube at a rotational orientation that partially or fully blocks flow into the cutting window 112 defined by the elongate shaft 108. In this way, the volume-controlled aspiration provided by the peristaltic pump 130 occurs partially or fully through the aperture 204 of the active electrode 114.

Figure 3:
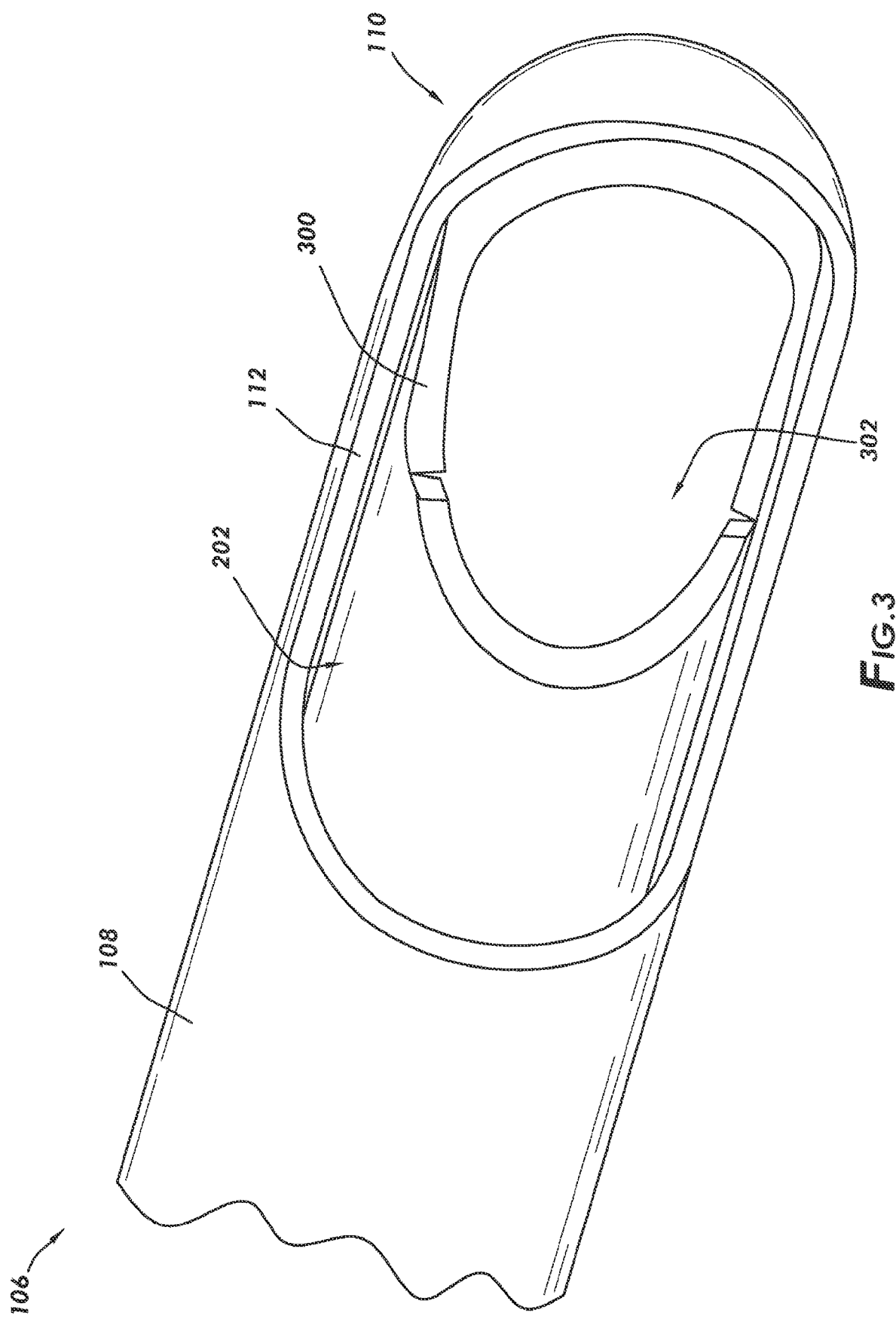
FIG. 3 shows a bottom perspective view of the distal end of the resection instrument in accordance with at least some embodiments.

FIG. 3 shows a bottom perspective view of the distal end 110 of the example resection instrument 106. In particular, visible in FIG. 3 is the cutting window 112, a portion of the elongate shaft 108, and the internal tube 202. In the view of FIG. 3, the internal tube 202 is at a rotational orientation at which the cutting window 300 of the internal tube 202 is aligned with the cutting window 112 of the elongate shaft 108. Because of the rotational alignment, also visible is the suction lumen 302 defined within the inside diameter of the internal tube 202 (and thus also within the inside diameter of the elongate shaft 108). During mechanical resection, the volume-controlled aspiration flow created by the peristaltic pump 130 (FIG. 1) draws fluid and tissue into the aligned cutting windows 112 and 300. As the internal tube 202 rotates, the interaction of the cutting windows 112 and 300 act to cut or resect the tissue disposed therein, and thus fluid and tissue fragments are aspirated or transported along the suction lumen defined by the resection instrument 106. In the example orientation shown the internal tube 202 blocks the aperture 204 (FIG. 2). At other points in the rotation of the internal tube 202, the cutting window 300 is aligned with the aperture 204 such that, momentarily, aspiration flow may move through the aperture 204 of the active electrode. However, the internal tube 202 may turn at several thousand revolutions per minute (RPM), and thus the aspiration through the active electrode 114 during mechanical resection is relatively low.

Figure 4:
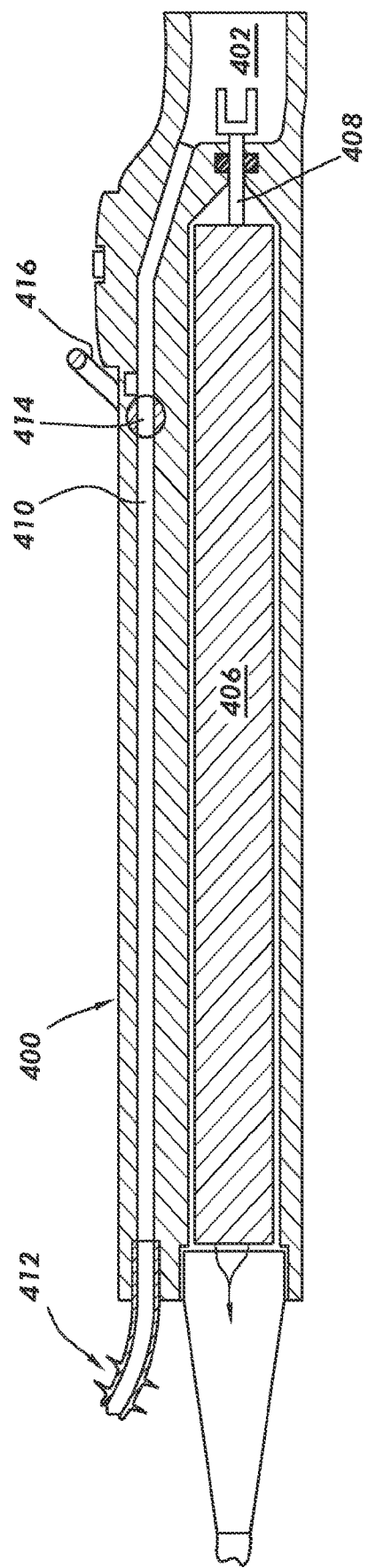
FIG. 4 shows a simplified cross-sectional view of a related-art handpiece.

Related-art handpieces comprise a valve within the aspiration pathway between the resection device and the source of suction, such as wall suction in a surgical room. During related-art mechanical resection procedures, the surgeon adjusts the flow rate along the aspiration pathway within the resection device by adjusting the valve position. FIG. 4 shows a simplified cross-sectional view of a related-art handpiece. In particular, FIG. 4 shows a portion of the outer housing 400 that defines a receptacle 402. Within the outer housing 400 resides a motor 406 defining a drive shaft 408. The drive shaft extends into the receptacle 402 and is coupled to an example drive fork. The related-art handpiece defines an aspiration pathway 410 from the receptacle 402 on the distal end to a tube connector 412 on the proximal end. Thus, fluid and tissue fragments aspirated through the resection device (not shown) flow along the aspiration pathway 410. The aspiration pathway 410 includes a valve member 414 coupled to an external valve handle 416. In the arrangement of FIG. 3, the valve member 414 is fully open. During related-art mechanical resection procedures, the surgeon adjusts the flow rate along the aspiration pathway 410 by adjusting the position of the valve member 414. When higher flow rates are desired, the surgeon opens the valve (as shown), and when lower flow rates are desired, the surgeon rotates the valve handle 416 and thus creates a constriction within the aspiration pathway 410 by way of the valve member 414.

Controlling aspiration flow rate using the valve member 414 may have drawbacks. For example, the constriction introduced to lower or limit the aspiration flow rate is subject to clogging by tissue resected by the resection device. It may take the surgeon many seconds to realize the aspiration flow has stopped and open the valve to clear the clog, if the clog can be cleared. Moreover, the once the clog is cleared the aspiration flow may jump to a flow rate higher than desired or expected by the surgeon. Moreover, the amount of aspiration flow is not a straight-line linear relationship to the position of the valve handle 416 over its span. In fact, at the "half-way" point of the travel of the valve handle 416, the valve may be almost fully closed. The non-linear relationship of the position of the valve handle 416 to the aspiration flow rate may make it difficult for the surgeon to achieve, or quickly achieve, the desired flow rate. Further still, the valve member 414 is subject to wear over time—for example, the edges at the boundaries of the valve member 414 may be worn over time, which changes the responsiveness of the aspiration flow rate to the position of the valve handle 416. Thus, a "new" related-art handpiece may have different responsiveness to position of the valve handle 416 than a handpiece nearing the end of its useful life. Moreover, related-art handpieces do not contemplate use with a resection instrument 106 that also performs ablation. Thus, if a related-art handpiece is used with a resection instrument 106 (FIG. 1), the position of the valve member 414 during ablation may adversely affect operation of the device.

Returning to FIG. 1. The issues noted above are addressed, at least in part, by the handpiece 116 and surgical controller 102 that controls the aspiration flow rate through the resection instrument 106 and the handpiece 116 using the peristaltic pump 130, rather than a controllable constriction within the aspiration pathway. More particularly, regardless of whether the surgeon implements mechanical resection or ablation, the aspiration flow rate through the resection tool 103 is controlled by speed of the peristaltic pump. In such cases, the handpiece 116 omits the valve member 414 (FIG. 4). More particularly, in various examples the surgical controller 102 is communicatively coupled to the interface device (illustratively shown as positional-interface device 118), and sets speed of the peristaltic pump based directly on the surgeon's interaction with the interface device. In various examples, the surgical controller 102 does not implement closed-loop control of the aspiration flow rate; rather, in various examples the aspiration flow rate is controlled exclusively by the surgeon's interaction with the interface device. The specification now turns to several example interface devices.

Figure 5A:
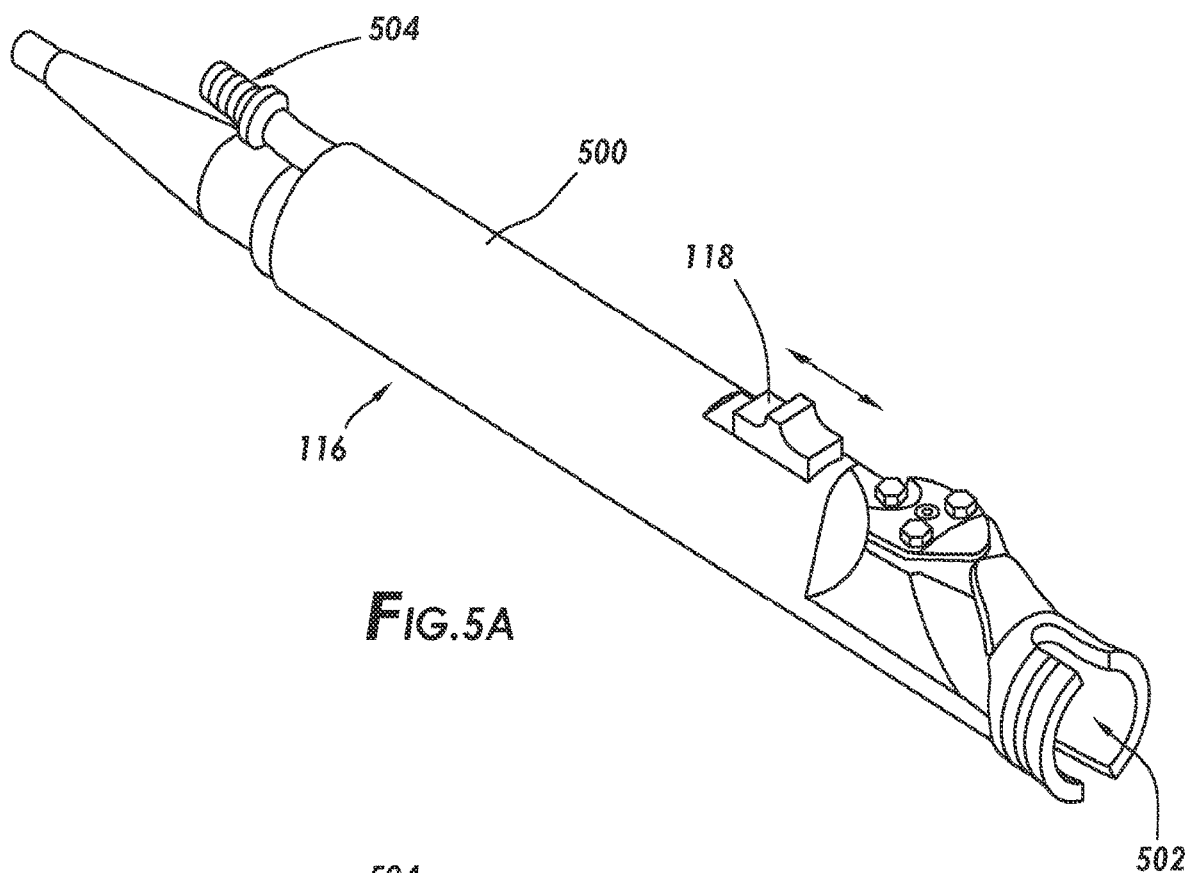
FIG. 5A shows a handpiece in accordance with at least some embodiments.

FIG. 5A shows an example handpiece 116. In particular, FIG. 5A shows the handpiece 116 comprises an outer housing 500. The outer housing 500 defines on the distal end a receptacle 502 into which a resection instrument 106 (FIG. 1) is telescoped. Coupling the resection instrument 106 into the receptacle 502 mechanically couples a rotor of a motor within the outer housing 500 to the internal tube 202 (FIG. 2) of the resection instrument 106. Moreover, coupling the resection instrument 106 into the receptacle 502 fluidly couples the suction lumen 302 (FIG. 3) of the resection instrument 106 to an aspiration pathway defined through the outer housing 500 and fluidly coupled to the tube connector 504 defined on the proximal end of the handpiece 116. In example cases, the handpiece 116 does not include a valve in the aspiration pathway between receptacle 502 and the tube connector 504.

The handpiece 116 further includes the interface device in the example form of the positional-interface device 118. In use, the surgical controller 102 (FIG. 1) reads positon of the positional-interface device 118 and controls or sets the speed of the peristaltic pump 130 (FIG. 1) based on the position of the positional-interface device 118. For example, as the surgeon slides the positional-interface device 118 toward the distal end of the handpiece 116, the surgical controller 102 increases the speed of the peristaltic pump 130. And oppositely, as the surgeon slides the positional-interface device 118 toward the proximal end of the handpiece 116, the surgical controller 102 decreases the speed of the peristaltic pump 130. In the case of mechanical resection, the speed of the peristaltic pump may be set at any point along the entire speed range (e.g., 10 to 400 RPM) of the peristaltic pump 130 by position of the positional-interface device 118. That is to say, the speed of the peristaltic pump 130 is set and controlled directly and exclusively by the position of the positional-interface device 118. For example: when the positional-interface device 118 is in its distal-most position, the surgical controller 102 (FIG. 1) sets the speed of peristaltic pump 130 at the upper limit of the range (e.g., 400 RPM); when the positional-interface device 118 is at a medial position along travel length, the surgical controller 102 sets the speed of peristaltic pump 130 in the middle of the speed range (e.g., about 200 RPM); and when the positional-interface device 118 is at a medial position along travel length, the surgical controller 102 sets the speed of peristaltic pump 130 at the lower limit of the speed range (e.g., 10 RPM).

In the case of ablation, several implementations are possible. In one example, the ablation may be implemented one of several modes, where the modes define an amount of energy supplied to the active electrode during ablation, and the speed of the peristaltic pump may be set at any point along the entire speed range (e.g., 10 to 400 RPM) by position of the positional-interface device 118. For example, in a "high" mode, energy in a high range may be provided to the active electrode and the surgeon modulates the speed of the peristaltic pump 130 over the entire speed range (e.g., 10 to 400 RPM) by position of the positional-interface device 118 by position of the positional-interface device 118. In a "medium" mode, energy in a medium range, lower than the high range, may be provided to the active electrode, and again the surgeon modulates the speed of the peristaltic pump 130 over the entire speed range (e.g., 10 to 400 RPM) by position of the positional-interface device 118. In a "low" mode, energy in a low range, lower than both the medium and high range, may be provided to the active electrode, and again the surgeon modulates the speed of the peristaltic pump 130 over the entire speed range (e.g., 10 to 400 RPM) by position of the positional-interface device 118. While operating in any of the example modes, increasing aspiration flow may increase the plasma instability therefore increase the concomitant coagulation rate, and oppositely decreasing the aspiration flow may decrease the plasma instability therefore decrease the concomitant coagulation rate. That is, adjusting the aspiration flow during ablation, regardless of mode, may not be to remove fluids or debris faster, although that may also occur; rather, adjusting aspiration flow during ablation tweaks or adjusts the tissue effect. In these example cases the speed of the peristaltic pump 130 is set and controlled directly and exclusively by the position of the positional-interface device 118 over the entire range of speeds for the peristaltic pump 130.

Still considering ablation, in other examples the speed of the peristaltic pump 130 may be set within a range of speeds by position of the positional-interface device 118, where the range of speeds is predetermined based on the mode of operation of the ablation. For example, in the example high mode the speed of the peristaltic pump 130 may set within a first predetermined range of speeds (e.g., 100 to 400 RPM), in the example medium mode the speed of the peristaltic pump 130 may be set within a second predetermined range of speeds (e.g., 60 to 250 RPM), and in the example low mode the speed of the peristaltic pump 130 may be set within a third predetermined range of speeds (e.g., 10 to 100 RPM). Here again, while operating in any of the example modes, increasing aspiration flow may increase the plasma instability therefore increase the concomitant coagulation rate, and vice versa. Thus, adjusting the aspiration flow during ablation, regardless of mode, may not be to remove fluids or debris faster, although that may also occur; rather, adjusting aspiration flow during ablation tweaks or adjusts the tissue effect. And note that while the example predetermined range of speeds of this paragraph overlap, each predetermined range of speeds is less than the entire range of pump speed of the peristaltic pump.

Figure 5B:
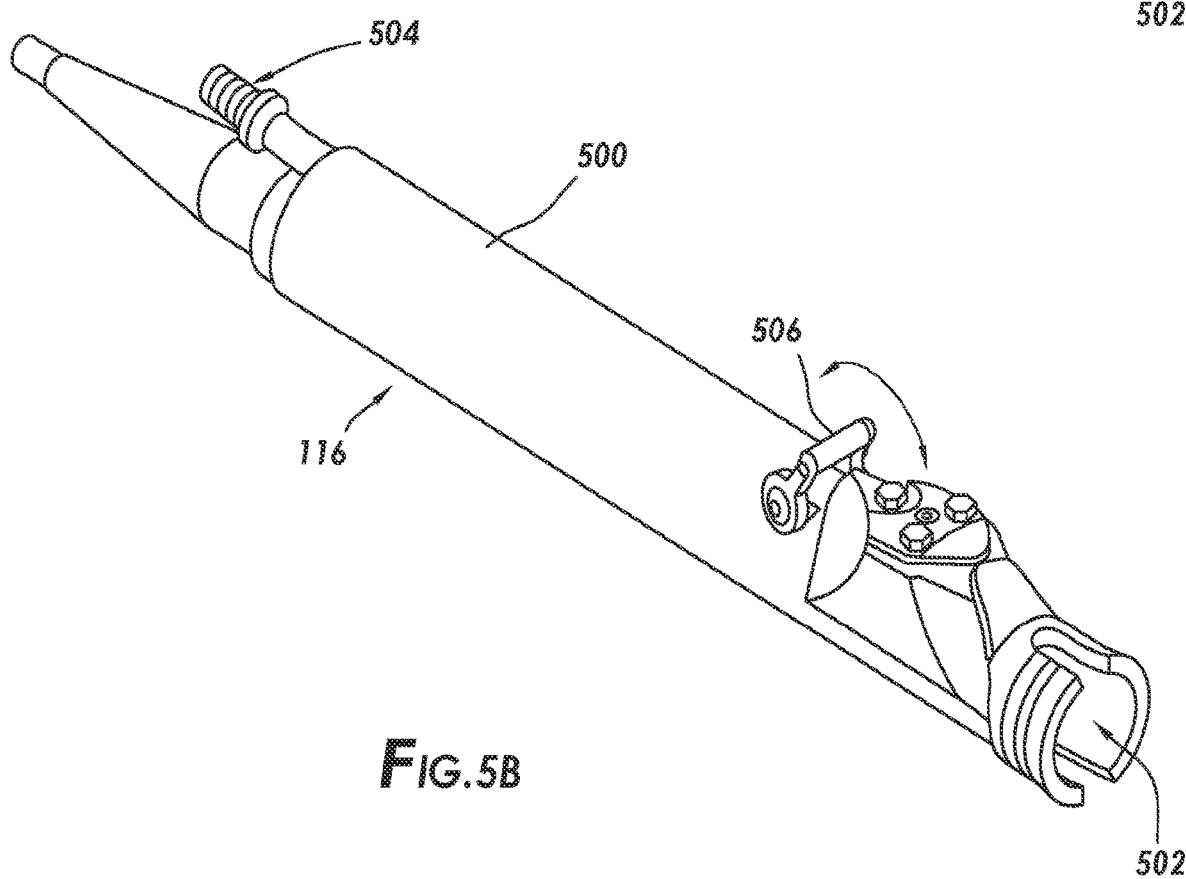
FIG. 5B shows a handpiece in accordance with at least some embodiments.

FIG. 5B shows another example handpiece 116. In particular, FIG. 5B shows the handpiece 116 again comprises the outer housing 500 and receptacle 502. Again in example cases, the handpiece 116 does not include a valve in the aspiration pathway between receptacle 502 and the tube connector 504. The handpiece 116 further includes the interface device in the example form of positional-interface device 506. The example positional-interface device 506 resembles the valve handle 416 (FIG. 4); however, the example positional-interface device 506 does not couple to an internal valve member. Rather, position of the positional-interface device 506 may be read by the surgical controller 102 (FIG. 1). In use, the surgical controller 102 reads positon of the positional-interface device 506 and controls or sets the speed of the peristaltic pump 130 (FIG. 1) based on the position of the positional-interface device 506. For example, as the surgeon rotates the example positional-interface device 506 toward the distal end of the handpiece 116, the surgical controller 102 increases the speed of the peristaltic pump 130. And oppositely, as the surgeon rotates the example positional-interface device 506 toward the proximal end of the handpiece 116, the surgical controller 102 decreases the speed of the peristaltic pump 130. In the case of mechanical resection and some ablation implementations, the speed of the peristaltic pump may be set at any point along the entire speed range of the peristaltic pump 130 by position of the positional-interface device 506. In other ablation implementations, the speed of the peristaltic pump 130 may be set within a range of speeds by position of the positional-interface device 506, where the range of speeds is predetermined based on a mode of operation of the ablation as discussed above.

The various interface devices discussed to this point are positional-interface devices in the sense that position of the device defines the speed of the peristaltic pump 130, and also visually indicates to the surgeon the pump speed setting. The specification now turns to example non-positional-interface devices.

Figure 5C:
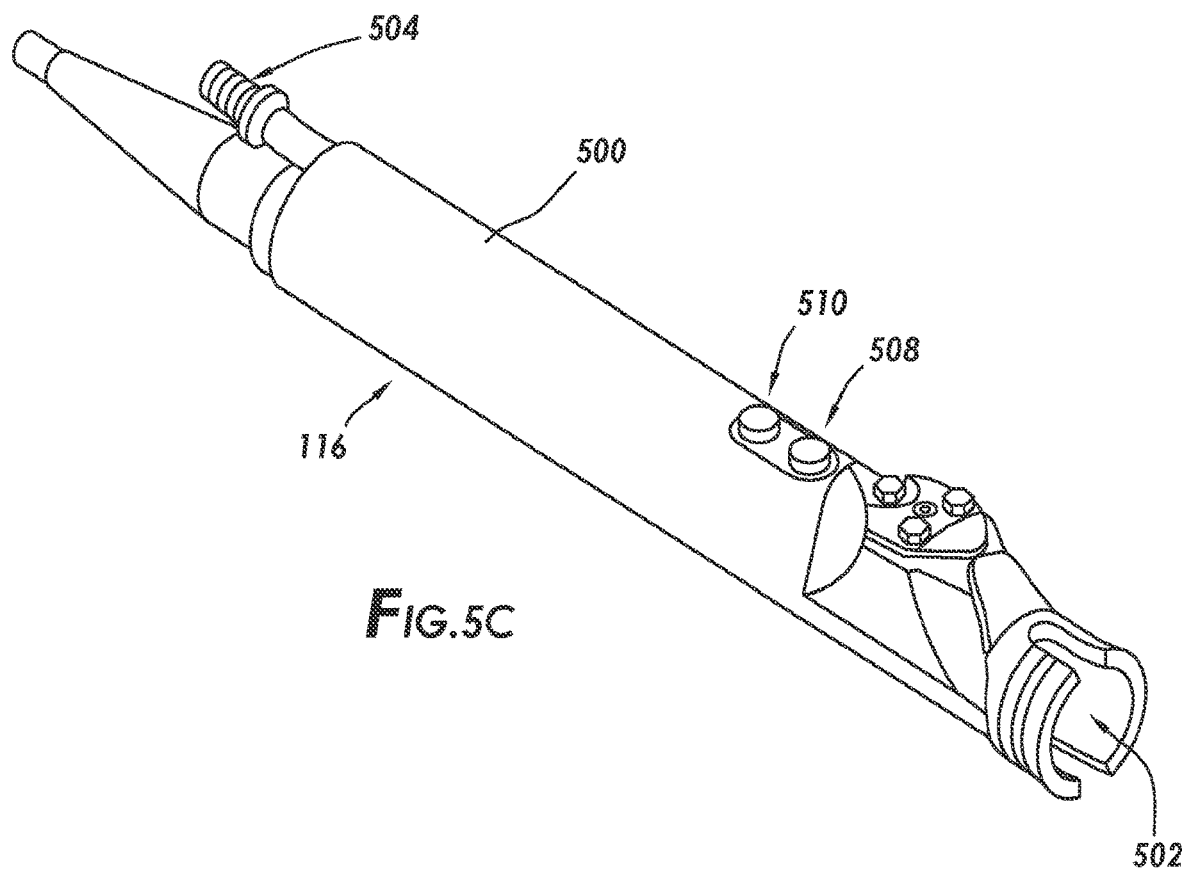
FIG. 5C shows a handpiece in accordance with at least some embodiments.

FIG. 5C shows another example handpiece 116. In particular, FIG. 5C shows the handpiece 116 again comprises the outer housing 500 and receptacle 502. Again in example cases, the handpiece 116 of FIG. 5C does not include a valve in the aspiration pathway between receptacle 502 and the tube connector 504. The handpiece 116 further includes the interface device in the example form of a set of buttons—illustratively an up button 508 and down button 510. Each of the buttons 508 and 510 may be momentary switches or momentary buttons that spring back to a rest position after each actuation. The surgical controller 102 (FIG. 1) may sense actuation of the up button 508 or the down button 510 in any suitable form. In use, the surgical controller 102 senses actuation of the buttons 508 and 510 and controls or sets the speed of the peristaltic pump 130 (FIG. 1) based on the actuations. For example, as the surgeon pushes or actuates the up button 508, the surgical controller 102 increases the speed of the peristaltic pump 130. And oppositely, as the surgeon pushes or actuates the down button 510, the surgical controller 102 decreases the speed of the peristaltic pump 130. That is to say, the speed of the peristaltic pump 130 is set and controlled directly and exclusively by actuation of the interface device in the form of the non-positional-interface devices shown as buttons 508 and 510.

In the case of mechanical resection and some ablation implementations, the speed of the peristaltic pump may be set at any point along the entire speed range of the peristaltic pump 130 by actuation of the buttons 508 and 510. In other ablation implementations, the speed of the peristaltic pump 130 may be set within a range of speeds by actuation of the buttons 508 and 510, where the range of speeds is predetermined based on the selected mode of operation of the ablation as discussed above. Stated otherwise, in example cases the speed of the peristaltic pump 130 is set and controlled directly and exclusively by actuation of non-positional-interface devices illustrative shown as buttons 508 and 510.

Figure 5D:
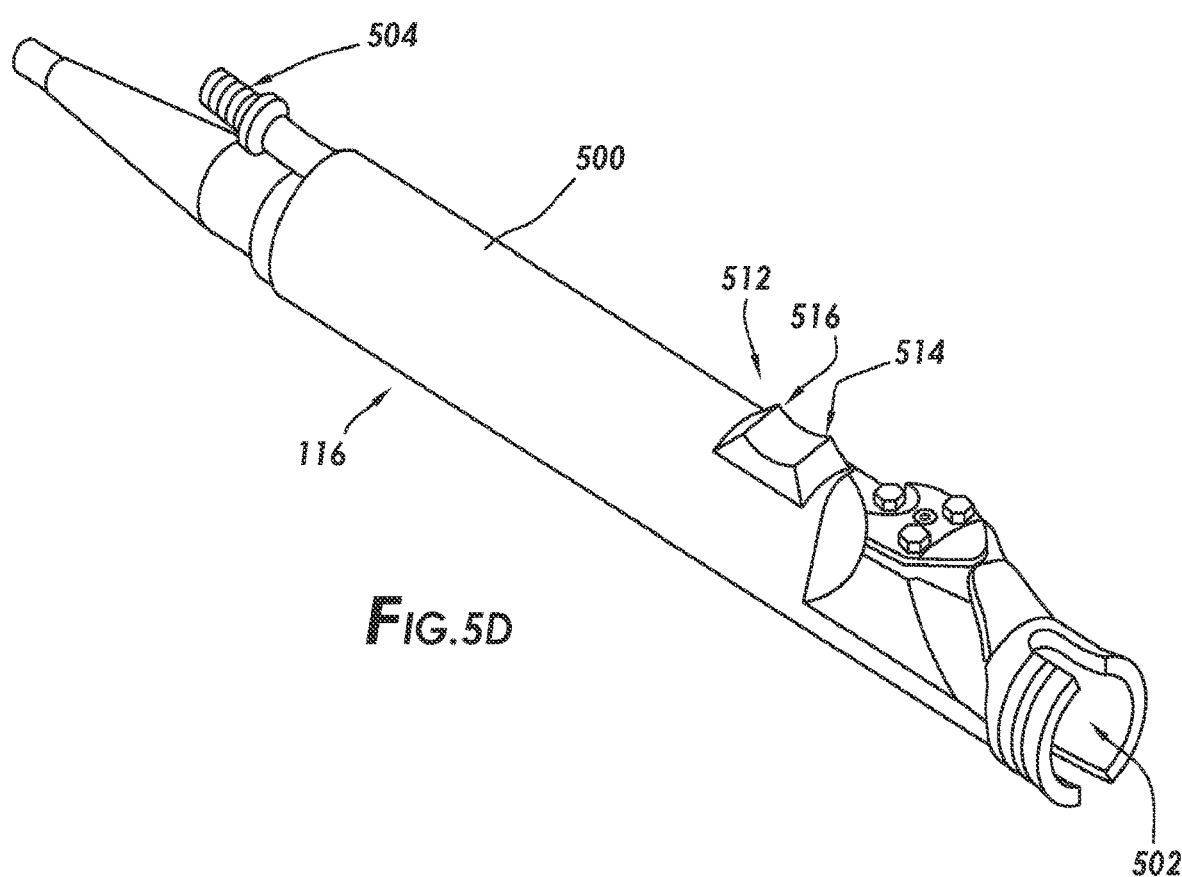
FIG. 5D shows a handpiece in accordance with at least some embodiments.

FIG. 5D shows another example handpiece 116. In particular, FIG. 5D shows the handpiece 116 again comprises the outer housing 500 and the receptacle 502. Again in example cases, the handpiece 116 of FIG. 5D does not include a valve in the aspiration pathway between receptacle 502 and the tube connector 504. The handpiece 116 further includes the interface device in the example form of a momentary rocker switch 512. In particular, the example momentary rocker switch 512 defines a rest orientation in which no Boolean signals are asserted. However, pushing downward on a distal end 514 of the momentary rocker switch 512 asserts an up actuation, and oppositely pushing downward on the proximal end 516 of the momentary rocker switch 512 asserts a down actuation. The momentary rocker switch 512 may spring back to its rest position after each actuation. The surgical controller 102 (FIG. 1) senses up actuation or down actuation in any suitable form. In use, the surgical controller 102 senses actuation of the momentary rocker switch 512 and sets the speed of the peristaltic pump 130 (FIG. 1) based on the actuations. For example, as the surgeon pushes or actuates the distal end 514 of the momentary rocker switch 512, the surgical controller 102 increases the speed of the peristaltic pump 130. And oppositely, as the surgeon pushes or actuates the proximal end 516 of the momentary rocker switch 512, the surgical controller 102 decreases the speed of the peristaltic pump 130. In the case of mechanical resection and some ablation implementations, the speed of the peristaltic pump may be set at any point along the entire speed range of the peristaltic pump 130 by actuation of the momentary rocker switch 512. In other ablation implementations, the speed of the peristaltic pump 130 may be set within a range of speeds by actuation of the momentary rocker switch 512, where the range of speeds is predetermined based on the selected mode of operation of the ablation as discussed above.

The interface devices discussed with respect to FIGS. 5A-5D are merely examples, and many variations are possible. For example, the interface device may be a knob devoid of positional markings and that turns about a rotation axis. Turning the knob in a first direction may result in speed of the peristaltic pump increasing, while turning the knob in a second direction opposite the first direction may result in speed of the peristaltic pump decreasing. Further still, the interface device may be a solid state component, such as capacitive touch sensor having a long dimension parallel to the longitudinal central axis of the handpiece 116. Thus, the surgeon may slide a finger along the touch sensor from the proximal end of the handpiece 116 toward the distal end of the handpiece 116 to indicate that the speed of the peristaltic pump should increase. And oppositely, the surgeon may slide a finger along the touch sensor from the distal end of the handpiece 116 toward the proximal end of the handpiece 116 to indicate that the speed of the peristaltic pump 130 should decrease. Knobs devoid of positional markings that indicate setting, capacitive touch sensors, Boolean interaction devices, and others like them, are examples of non-positional-interface devices as previously defined.

As alluded to above, the example surgical system 100 may switch between mechanical resection and ablation at the discretion of the surgeon. Implementing the interface device in the form of a non-positional-interface device enables additional features that may not be present when the interface device is a positional-interface device. In particular, consider a situation in which the surgical system 100 is in use for mechanical resection, and then the surgeon elects to transition to ablation. In such situations, the surgical controller 102 may stop the motor of the handpiece 116 (e.g., at a predetermined rotational position—such as with the cutting window closed). Then, the surgical controller 102 may provide electrical energy to the active electrode 114. However, because the non-positional-interface device does not have a position or orientation that directly indicates a speed of the peristaltic pump 130, the surgical controller 102 may set the speed of the peristaltic pump 130 in the newly instituted ablation in several different ways. In one case, the surgical controller 102 may set the speed at an initial or default speed. In other cases, the surgical controller 102 may set the speed to be the same speed as an immediately previous ablation. Setting the speed at an initial or default speed upon entering ablation, and/or setting the speed to be the same as a previous ablation upon entering an ablation, shall not be considered automatic or closed-loop speed control. Thereafter, the surgical controller 102 may modulate the speed of the peristaltic pump 130 responsive to the surgeon's interaction with the interface device.

Now consider a situation in which the surgical system 100 is in use for ablation, and then the surgeon elects to transition to mechanical resection. In such situations, the surgical controller 102 may cease the providing electrical energy to the active electrode 114, and then drive the motor within the handpiece 116 to cause mechanical resection of tissue. As part of the mechanical resection, the surgical system 100 may also aspirate fluid and tissue fragments through the suction lumen of the resection instrument 106. However, because the non-positional-interface device does not directly indicate a speed of the peristaltic pump 130, the surgical controller 102 may set the speed of the peristaltic pump 130 in the newly instituted mechanical resection in several different ways. In one case, the surgical controller 102 may set the speed at an initial or default speed. In other cases, the surgical controller 102 may set the speed to be the same speed as an immediately previous mechanical resection. Thereafter, the surgical controller 102 may modulate the speed of the peristaltic pump 130 responsive to the surgeon's interaction with the interface device.

FIG. 6 shows a block diagram of an example surgical system 100. In particular, FIG. 6 shows an electrosurgical controller 600, a peristaltic pump controller 602, and a resection controller 604. In some example surgical systems, the electrosurgical controller 600, the peristaltic pump controller 602, and the resection controller 604 are separate and distinct components that are communicatively coupled. In the example surgical system 100, however, the functionality of the electrosurgical controller 600, the peristaltic pump controller 602, and the resection controller 604 are implemented by and/or contained within the surgical controller 102. The balance of the discussion is based on the surgical controller 102 with the combined functionality.

The example surgical controller 102 comprises a processing device 606, an electrosurgical generator 608, a pump motor driver 610, a peristaltic pump 130 and a peristaltic motor 624 (shown as a single element), and a resection motor driver 614. The electrosurgical generator 608 is communicatively coupled to the processing device 606. The electrosurgical generator 608 defines an active terminal 616 coupled to an electrical pin or terminal 618 in the connector 142, and a return terminal 620 coupled to a return pin or terminal 622 in the connector 142. Though not show in the FIG. 6, the ablation connector 140 (FIG. 1) is configured to mechanically and electrically couple to the connector 142, and thus electrically couple the active electrode 114 (FIG. 1) and a return electrode (e.g., the elongate shaft 108) to the electrosurgical generator 608. The processing device 606 may command the electrosurgical generator 608 to provide electrical energy to the active electrode 114 to cause an electrosurgical outcome, such as ablation of tissue proximate to the active electrode 114, or coagulation of blood associated with tissue. Additional terminals may be present in the connector 142 (e.g., for additional active electrodes), but such additional terminals are not shown so as not to further complicate the figure.

The pump motor driver 610 is communicatively coupled to the processing device 606. The pump motor driver 610 is also coupled to the peristaltic motor 624 and peristaltic pump 130. The peristaltic motor 624 may take many forms, and thus the pump motor driver 610 may take many forms. For example, the peristaltic motor 624 may be an alternating current (AC) motor with a drive shaft coupled to the peristaltic pump 130, and thus the pump motor driver 610 may be a variable frequency AC motor driver. In other cases, the peristaltic motor 624 may be a direct current (DC) motor coupled to the peristaltic pump 130, and thus the pump motor driver 610 may be a variable voltage DC motor driver. Further still, the peristaltic motor 624 may be a stepper motor coupled to the peristaltic pump 130, and thus the pump motor driver 610 may be a stepper motor driver. Other peristaltic motor 624 types, and thus other pump motor drivers 610, may be used. Regardless of the precise type of peristaltic motor 624, in example systems the processing device 606 may command the pump motor driver 610 to drive the peristaltic pump 130 at a particular speed. More particularly, in example cases the processing device 606 sets and controls a speed setpoint provided to the pump motor driver 610 based on position and/or actuation of the interface device defined on and/or by the handpiece 116 (FIG. 1), and the pump motor driver 610 in turn drives the peristaltic motor 624 at the selected speed.

The resection motor driver 614 is communicatively coupled to the processing device 606. Moreover, the resection motor driver 614 is coupled to one or more electrical pins or motor terminals in the connector 126, illustratively shown as motor terminal 626. The number of additional motor terminals to which the resection motor driver 614 may couple depends on the type of motor implemented in the handpiece 116 (FIG. 1). The motor implemented in the handpiece 116 may take many forms, and thus the resection motor driver 614 may take many forms. For example, the motor implemented in the handpiece 116 may be an AC motor, and thus the resection motor driver 614 may be a variable frequency AC motor driver. In other cases, the motor implemented in the handpiece 116 may be a DC motor coupled, and thus the resection motor driver 614 may be a variable voltage DC motor driver. Further still, the motor implemented in the handpiece 116 may be a stepper motor, and thus the resection motor driver 614 may be a stepper motor driver. Other types of motors may be implemented in the handpiece 116, and thus other resection motor drivers 614, may be used.

Regardless of the precise type of motor implemented in the handpiece 116, in example systems the processing device 606 commands the resection motor driver 614 to drive the motor in the handpiece 116 to cause resection of tissue. In other cases, such as when the surgical controller 102 is transitioning from mechanical resection to ablation or coagulation, the processing device 606 commands the resection motor driver 614 to stop the motor implemented in handpiece 116 at a rotational position such that the cutting element of the resection instrument 106 (FIG. 1) is partially or fully blocked. For example, the handpiece 116 may implement Hall-effect sensors, and the resection instrument 106 may implement magnets on the rotating elements such that rotational position of the internal tube 202 (FIG. 2) relative to the elongate shaft 108 may be determined. For example, U.S. patent application Ser. No. 17/315,840 filed May 10, 2021 titled "Systems and Methods of Determining Orientation of Cutting Windows of a Mechanical Resection Instrument," incorporated by reference herein as if reproduced in full below, discusses several arrangements for determining the rotational orientation of the cutting element of the resection instrument. Thus, the processing device 606 may be communicatively coupled to sensors (e.g., Hall-effect sensors) within the handpiece 116 and use the information to stop the internal tube 202 at an appropriate rotational orientation. In other cases, the resection motor driver 614 implements sufficient processing capability such that the processing device 606 provides an indication of a stop position, and the resection motor driver 614 drives the motor in the handpiece 116 and stops the motor to implement the selected stop position.

Still referring to FIG. 6, in example systems the speed of the peristaltic pump 130 is controlled or modulated responsive to the surgeon's interaction with the interface device defined on the handpiece 116 (FIG. 1). Thus, in example cases the surgical controller 102, and particularly the processing device 606, receives commands from the interface device through the connector 126. FIG. 6 shows one example electrical arrangement through which the processing device 606 may receive or read information regarding the interface device. More particularly, FIG. 6 shows an example potentiometer 628 as the mechanism to sense surgeon's interaction with the interface device. In example cases, the potentiometer 628 is disposed within the resection tool 103, such as the handpiece 116, and the potentiometer 628 is operational coupled to the interface device. Consider that the interface device is the positional-interface device 118 of FIG. 1 (e.g., a slider). In the example system, a first connection or lead of the potentiometer 628 is coupled through a pin or terminal of the connector 126 to voltage source provided within the surgical controller 102. A second connection or lead of the potentiometer 628 is coupled through a pin or terminal of the connector 126 to a reference voltage (e.g., ground or common) within the surgical controller 102. A wiper 630 of the potentiometer 628 is coupled to the processing device 606 through a pin or terminal of the connector 126. Thus, in the example system the processing device 606 reads a voltage indicative of position of the example positional-interface device 118. Use of potentiometer as the mechanism to read position of a positional-interface device is merely an example. Other mechanisms include proximity sensors, optical measurement systems, and packet-based message systems where a processing device within the handpiece 116 makes a position measurement in some form, and sends the position information to the processing device 606 by way of packet based communications. An example of communicatively coupling to a non-positional-interface device is discussed in more detail below.

The example surgical controller 102 further defines the connector 154. Though not show in FIG. 6, the pedal connector 152 (FIG. 1) is configured to mechanically and electrically couple to the connector 154, and thus electrically couple the foot pedal devices 144, 146, and/or 148 to the processing device 606. The processing device 606 thus receives commands regarding activation and deactivation of the electrosurgical generator 608, and likewise receives commands regarding activation and deactivation of the resection motor driver 614.

FIG. 7 shows a block diagram of an example surgical system. In particular, FIG. 7 shows an example surgical controller 102 having many of the same components as in FIG. 6, and thus those components are not introduced again so as not to unduly lengthen the discussion. FIG. 7, however, shows an example system in which the interface device of the handpiece 116 (FIG. 1) implements a non-positional-interface device (e.g., as shown in FIG. 5C or 5D). More particularly, non-positional-interface devices comprise momentary push buttons, such as up button 508 (FIG. 5C) and down button 510 (FIG. 5C), and/or momentary rocker switches, such as momentary rocker switch 512 (FIG. 5D). These example non-positional-interface devices are Boolean devices in the sense that the surgeon's interaction with the interface devices creates Boolean signals read by the processing device 606. However, non-positional-interface devices also comprise "analog" devices (e.g., knobs, rollers) whose implied setpoint is not apparent from the position or makings on the devices.

FIG. 7 illustrates non-positional-interface devices that create Boolean signals as momentary switches 700 and 702. In particular, momentary switch 700 defines a first lead or connection coupled to a reference voltage (e.g., ground or common) through the connector 126, and a second lead or connection coupled to a pull-up resistor 704 and the processing device 606. Similarly, momentary switch 702 defines a first lead or connection coupled to the reference voltage through the connector 126, and a second lead or connection coupled to a pull-up resistor 706 and the processing device 606. It follows that in the example the processing device 606 may read Boolean signals indicative of position of the momentary switches 700 and 702. Considering momentary switch 700 as representative, in the rest or non-asserted state, the momentary switch 700 is open or non-conductive and thus the voltage sensed by the processing device 606 will be the high. However, when the momentary switch 700 is pressed or asserted, the second lead of the pull-up resistor 704 is grounded, and thus the processing device 606 senses a low voltage (e.g., the Boolean signal sensed by the processing device 606 is asserted low). The arrangement of FIG. 7 is merely an example, and other arrangements for electrically coupling the example momentary switches 700 and 702 are possible, including arrangements in which the signals sensed by the processing device 606 are asserted high, and arrangements in which the state of the momentary switches 700 and 702 are sensed by a processing device within the handpiece and communicated using packet-based messages. Further still, the electrical momentary switches 700 and 702 may be replaced with optical systems in which actuation changes the state of light propagating through an aperture.

The processing device 606 may take any suitable form. In some cases, the processing device 606 may be an application specific integrated circuit (ASIC) designed and read various inputs and control the electrosurgical generator 608, the pump motor driver 610, and/or the resection motor driver 614. In other cases, the processing device 606 may be a processor-type device, such as a microcontroller with controlling software, a reduced-instruction-set computing (RISC) with controlling software, a digital signal processor (DSP), and/or a processor with controlling software, the controlling software in each case designed and constructed to read various inputs and control the electrosurgical generator 608, the pump motor driver 610, and/or the resection motor driver 614. In addition to or in place of the above, the processing device 606 may implement a programmable logic device (PLD) or a field programmable gate array (FPGA), configured to read various inputs and control the electrosurgical generator 608, the pump motor driver 610, and/or the resection motor driver 614. Further still, the processing device 606 may be or include individual circuit components designed and constructed to read various inputs and control the electrosurgical generator 608, the pump motor driver 610, and/or the resection motor driver 614.

The specification now turns to various operational techniques in accordance with various examples. Referring simultaneously to FIGS. 1 and 6, consider first that the surgical system 100 is being used for mechanical resection of tissue. In such circumstances, the surgical system 100 is designed and constructed to drive the motor within the handpiece 116 to cause resection of tissue by the resection instrument 106, the driving by way of the resection motor driver 614 of the surgical controller 102. While resecting tissue, the example surgical system 100 aspirates fluid and tissue fragments through the suction lumen of the resection instrument 106. That is, the surgical system 100 drives the peristaltic pump 130 by way of the pump motor driver 610 to cause the aspiration of fluid and tissue fragments. During such resection and aspiration, the surgical system 100 modulates speed of the peristaltic pump 130 responsive to the surgeon's interaction with the interface device, such a positional-interface device or non-positional interface device. Stated otherwise, in example cases the speed of the peristaltic pump 130 is set and controlled directly and exclusively by interaction with the interface device.

For example, the surgical system 100, and particularly the processing device 606 of the example surgical controller 102, may read the positional-interface device 118, and the reading results in data indicative of position. Based on the data indicative of position, the processing device 606 sets the speed of the peristaltic pump 130 by communication to the pump motor driver 610. In the case of resection of tissue and some ablation implementations, the speed of the peristaltic pump 130 may be set within a range of speeds, such as an entire operational range of speeds (e.g., 10 RPM to 400 RPM). As another example, the surgical system 100, and particularly the processing device 606 of the surgical controller 102, may receive an indication of actuation of the interface device in the form of a non-positional-interface device, such as an up button (e.g. momentary switch 700), a down button (e.g., momentary switch 702), and/or interaction with the momentary rocker switch 512. Again in the case of resection of tissue and some ablation implementations, the speed of the peristaltic pump 130 may be set within a range of speeds, such as an entire operational range of speeds (e.g., 10 RPM to 400 RPM), by the non-positional-interface devices. For example, in the case of actuation of the up button, the processing device 606 increases speed of the peristaltic pump 130 by communication to the pump motor driver 610, and oppositely in the case of actuation of the down button, the processing device 606 decreases speed of the peristaltic pump 130 by communication to the pump motor driver 610.

Now consider that the surgical system 100 is being used for ablation and/or coagulation using the active electrode 114. In such circumstances, the surgical system 100 is designed and constructed to arrange the resection instrument 106 such that the cutting window 112 is partially or fully blocked. In particular, the processing device 606 may command the resection motor driver 614 to stop the internal tube to a particular rotational orientation. Once the resection instrument 106 is mechanically arranged, the surgical system 100, and particularly the processing device 606 surgical controller 102, commands the electrosurgical generated 608 to provide electrical energy to the active electrode 114, where the electrical energy causes ablation of tissue and/or coagulation. During the application of electrical energy, the surgical system 100 is designed and constructed to draw, by way of the peristaltic pump 130, fluid and tissue fragments through the suction lumen of the resection instrument 106. In some cases, at least a portion of the fluid and/or tissue is drawn through the aperture 204 (FIG. 2) of the active electrode 114.

In example ablations, the surgical system 100 may implement various modes of operation. For example, the surgeon may interact with the processing device 606 by way of the buttons 120 to set a mode of operation (e.g., high, medium, or low). In other examples, the surgeon may interact with the processing device 606 by way of the interface device 145 to select a mode of operation. For example, by interacting with the interface device 145 in the form of a touch screen the surgeon communicates a selected mode of operation of the ablation to the processing device 606. In yet still further examples, by interacting with the foot pedal assembly 104 the surgeon communicates a selected mode of operation of the ablation to the processing device 606.

The mode of operation for ablation may be related to aggressiveness of the ablation. In an example "high" mode, a high amount of energy may be provided to the active electrode. The example high mode may be used for bulk removal of tissue, such as to quickly clear an area (e.g., notchplasty during a replacement of the anterior cruciate ligament (ACL)). In some cases, within the high mode the interface device may be used to modulate the speed of the peristaltic pump across the entire range of speeds of the peristaltic pump. In other cases, the example high mode may also include a high predetermined range of speeds (e.g., 100 to 400 RPM) within which the peristaltic pump 130 operates during the high mode. In such cases during the high mode, the interface device may be used to modulate the speed of the peristaltic pump 130 within the range of speeds defined by the high mode.

Oppositely, in an example "low" mode, a low amount of energy may be provided to the active electrode, lower than both the high mode and the medium mode. The example low mode may be used for fine sculpting of tissue. In some cases, within the low mode the interface device may be used to modulate the speed of the peristaltic pump across the entire range of speeds of the peristaltic pump. In other cases, the example low mode may also include a low predetermined range of speeds (e.g., 10 to 100 RPM) within which the peristaltic pump 130 operates during the low mode. In such cases during the low mode, the interface device may be used to modulate the speed of the peristaltic pump 130 within the range of speeds defined by the low mode.

In the middle between high mode and low mode, the example system may implement a "medium" mode. In the medium mode, in the medium mode a medium amount of energy may be provided to the active electrode, the energy in the medium mode between the energies of the high mode and medium mode. In some cases, within the medium mode the interface device may be used to modulate the speed of the peristaltic pump across the entire range of speeds of the peristaltic pump. In other cases, the example medium mode may also include a low predetermined range of speeds (e.g., 60 to 250 RPM) within which the peristaltic pump 130 operates during the medium mode. In such cases during the medium mode, the interface device may be used to modulate the speed of the peristaltic pump 130 within the range of speeds defined by the medium mode.

In cases in which the modes of ablation also implement predefined range of speeds, the following correlates the information in table form.

TABLE 1

| Mode | Pump Speed (RPM) |
| --- | --- |
| High | 100-400 |
| Medium | 60-250 |
| Low | 10-100 |

Thus, in example systems the processing device 606 of the surgical controller 102 receives an indication of a mode of operation selected from a plurality of modes of operation. In example systems in which each the mode of operation includes predefined range of pump speeds, the mode selection defines and implements a predetermined range of pump speeds, each range of pump speeds less than an entire range of pump speed of the peristaltic pump. Additionally in these examples, the surgical system 100, and particularly the processing device 606 of the surgical controller 102, is designed and constructed to modulate speed of the peristaltic pump 130 within the range of pump speeds defined by the mode of operation responsive to the surgeon's interaction with the interface device.

Considering cases in which the each mode of operation includes a predefined range of pump speeds, the surgical system 100, and particularly the processing device 606 of the surgical controller 102, may read the positional-interface device 118, and the reading results in data indicative of position. Based on the data indicative of position, the processing device 606 of the surgical controller 102 sets speed of the peristaltic pump 130 within range defined by the mode of operation. As another example, the surgical system 100, and particularly the processing device 606 of the surgical controller 102, may receive an indication of actuation of the interface device in the form of a non-positional-interface device, such as an up button (e.g. momentary switch 700), a down button (e.g., momentary switch 702), and/or interaction with the momentary rocker switch 512. In the case of actuation of the up button, the processing device 606 increases speed of the peristaltic pump 130 within the range defined by the mode of operation by communication with the pump motor driver 610. Oppositely, in the case of actuation of the down button, the processing device 606 decreases speed of the peristaltic pump 130 within the range defined by the mode of operation by communication with the pump motor driver 610.

The example surgical system 100 switches between mechanical resection and ablation at the discretion of the surgeon. Implementing the interface device in the form of a non-positional-interface device enables additional features. In particular, consider a situation in which the surgical system 100 is in use for mechanical resection, and then the surgeon elects to transition to ablation. In such situations, the processing device 606 surgical controller 102 may stop the motor of the handpiece 116 at a rotational position such that the cutting window 112 is at least partially blocked. Then, the processing device 606 of the surgical controller 102 may command the electrosurgical generator 608 to provide electrical energy to the active electrode 114. However, because the non-positional-interface device does not directly indicate a speed of the peristaltic pump 130, the processing device 606 of the surgical controller 102 may set the speed of the peristaltic pump 130 in the newly instituted ablation in several different ways. In one case, the processing device 606 of the surgical controller 102 may set the speed at an initial or default speed (e.g., in the middle of the speed range for the selected mode of operation). In other cases, the processing device 606 of the surgical controller 102 may set the speed to be the same speed as previous ablation (e.g., the immediately previous ablation). Thereafter, the processing device 606 of the surgical controller 102 may modulate the speed of the peristaltic pump 130 responsive to the surgeon's interaction with the interface device.

Now consider a situation in which the surgical system 100 is in use for ablation and/or coagulation, and then the surgeon elects to transition to mechanical resection. In such situations, the processing device 606 of the surgical controller 102 may command the electrosurgical generator 608 to cease providing electrical energy to the active electrode 114, and then the processing device 606 of the surgical controller 102 may command the resection motor driver 614 to drive the motor within the handpiece 116, and further command the pump motor driver 610 to drive the peristaltic pump 130 to aspirate fluid and tissue fragments through the suction lumen of the resection instrument 106. However, because the non-positional-interface device does not directly indicate a speed of the peristaltic pump 130, the processing device 606 of the surgical controller 102 may set the speed of the peristaltic pump 130 in the newly instituted mechanical resection in several different ways. In one case, the processing device 606 of the surgical controller 102 may set the speed at an initial or default speed (e.g., in the middle of the entire speed range of the peristaltic pump 130). In other cases, the processing device 606 of the surgical controller 102 may set the speed to be the same speed as a previous mechanical resection (e.g., the immediately previous mechanical resection). Thereafter, the processing device 606 of the surgical controller 102 may modulate the speed of the peristaltic pump 130 responsive to the surgeon's interaction with the interface device.

Returning briefly to FIG. 1. The various examples provided to this point are based on the resection tool 103 comprising the handpiece 116 designed and constructed implement a motor that turns the internal tube of the resection instrument 106, and where that resection instrument 106 further includes the active electrode 114 with which ablation and/or coagulation may be performed. In the example systems, regardless of whether the system is performing mechanical resection or ablation/coagulation, the aspiration flow rate of fluid and tissue fragments is set and directly controlled by the interface device (such as positional-interface device 118) defined on and by the handpiece 116. The example handpiece 116 may also be used with a resection instrument that only performs mechanical resection, and in those situations as well the aspiration flow rate may be controlled by the interface device. Oppositely, the surgical system 100 need not implement mechanical resection in all cases, and may implement ablation/coagulation only.

Figure 8:
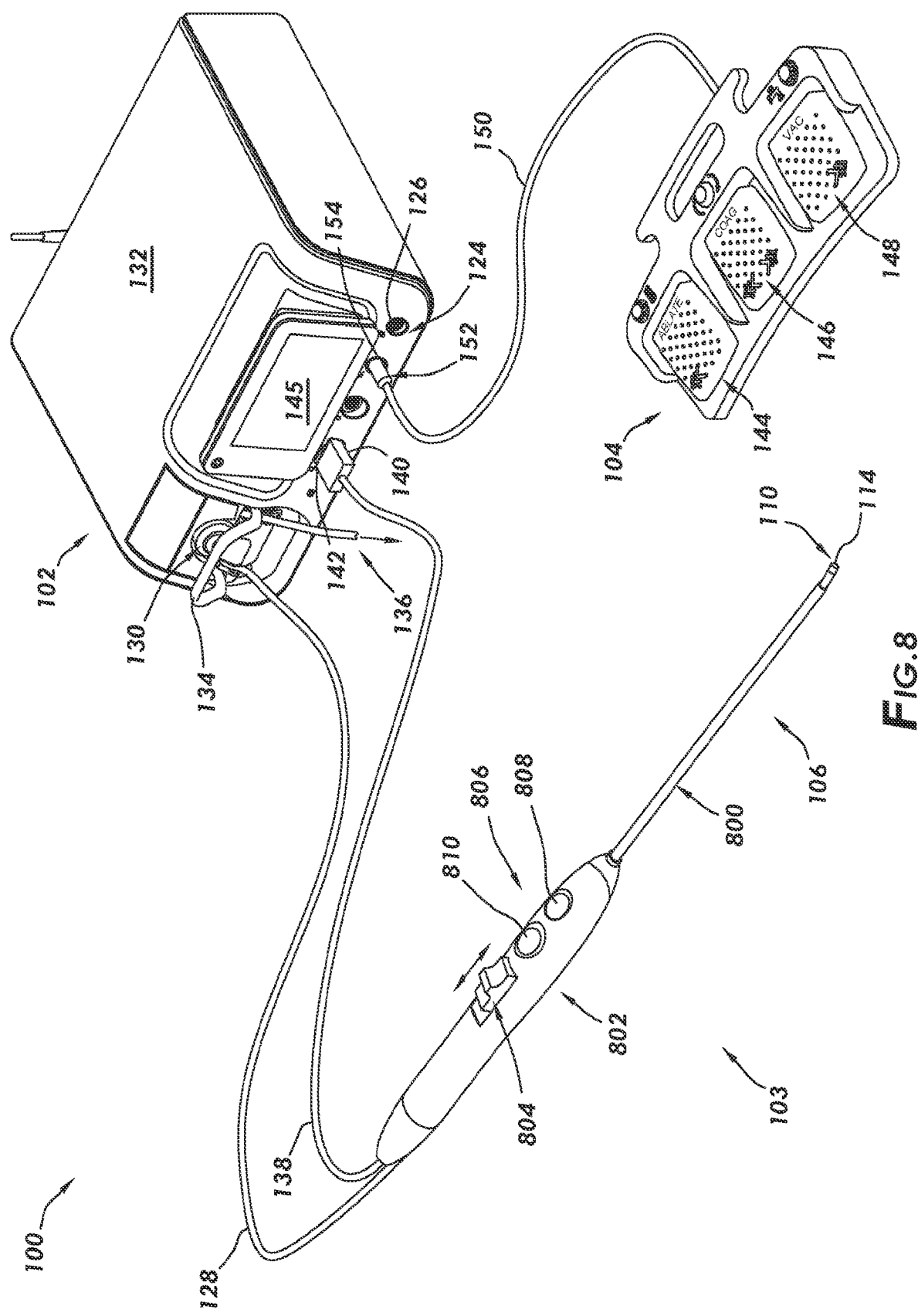
FIG. 8 shows a surgical system 100 in accordance with at least some embodiments.

FIG. 8 shows another example surgical system 100. In particular, the surgical system 100 comprises the surgical controller 102, the resection tool 103, and the foot pedal assembly 104. In this case, however, the resection tool 103 performs ablation and/or coagulation, and the resection tool 103 does not and cannot perform mechanical resection. More particularly, the resection tool 103 comprises an elongate shaft 800 that defines distal end 110. The resection tool 103 further defines a handle 802 at the proximal end of the elongate shaft 800, the handle 802 being where a surgeon grips the resection tool 103 during surgical procedures. The resection tool 103 further comprises the flexible multi-conductor cable 138 housing one or more electrical leads (not specifically shown) and terminating in the ablation connector 140. By way of the multi-conductor cable 138, the surgical controller 102 may provide electrical energy to the active electrode 114 for electrically-based ablation and/or coagulation. Moreover, the multi-conductor cable 138 may provide an electrical return path for the electrical circuit (e.g., the elongate shaft 800 may act as the return electrode for electrically-based procedures). Though not visible in the view of FIG. 8, the elongate shaft 800 defines an internal fluid conduit or suction lumen fluidly coupled to the flexible tubular member 128. As before, the tubular member 128 is coupled to the peristaltic pump 130.

The example resection tool 103 further defines an interface device illustratively shown as positional-interface device 804 defined on an exterior surface of the handle 802. During use, and as discussed above, the surgeon may use the example positional-interface device 804 to set or select an aspiration flow rate through a suction lumen of the resection tool 103 (e.g., through the internal diameter of the elongate shaft 800). The example resection tool 103 further defines additional buttons on the upper surface, such as buttons 806. The surgeon may interact with buttons 806 to set or select various operational parameters, such as the mode of operation of ablation as discussed above, or to toggle between an ablation mode and a non-ablative coagulation mode.

In example systems, surgical controller 102 controls the aspiration flow rate through the resection tool 103 using the peristaltic pump 130. More particularly, the aspiration flow rate through the resection tool 103 is controlled by speed of the peristaltic pump 130, and the example resection tool 103 does not include valve member within the aspiration pathway. More particularly still, in various examples the surgical controller 102 is communicatively coupled to the interface device (illustratively shown as positional-interface device 804), and sets speed of the peristaltic pump based directly on the surgeon's interaction with the interface device. In yet still further cases, the positional-interface device 804 may be omitted, and the buttons 806 may thus be used as non-positional-interface devices to directly control or set the speed of the peristaltic pump 130.

In use, the surgical controller 102 (FIG. 1) reads positon of the positional-interface device 804 and controls or sets the speed of the peristaltic pump 130 based on the position of the positional-interface device 804. For example, as the surgeon slides the positional-interface device 118 toward the distal end of the handle 802, the surgical controller 102 increases the speed of the peristaltic pump 130. And oppositely, as the surgeon slides the positional-interface device 804 toward the proximal end of the handle 802, the surgical controller 102 decreases the speed of the peristaltic pump 130. The speed range controlled by the example positional-interface device 804 may be the entire speed range of the peristaltic pump 130, or may be within predefined speed ranges associated with a selected mode of operation, all as discussed above. While the example positional-interface device 804 is illustratively shown as a slider, the positional-interface device may take any suitable form as discussed above (e.g., resembling a valve handle as in FIG. 5B, but not associated with an internal valve member).

In examples in which the buttons 806 are used as non-positional-interface devices (and the positional-interface device 804 is not implemented), buttons 806 may define up button 808 and down button 810. Each of the buttons 808 and 810 may be momentary switches or momentary buttons that spring back to a rest position after each actuation. The surgical controller 102 may sense actuation of the up button 808 or the down button 810 in any suitable form. In use, the surgical controller 102 senses actuation of the buttons 808 and 810 and controls or sets the speed of the peristaltic pump 130 (FIG. 1) based on the actuations. For example, as the surgeon pushes or actuates the up button 508, the surgical controller 102 increases the speed of the peristaltic pump 130. And oppositely, as the surgeon pushes or actuates the down button 510, the surgical controller 102 decreases the speed of the peristaltic pump 130. That is to say, the speed of the peristaltic pump 130 is set and controlled directly and exclusively by actuation of the interface device in the form of the non-positional-interface devices shown as buttons 808 and 810. For example, as the surgeon pushes the up button 808, the surgical controller 102 increases the speed of the peristaltic pump 130. And oppositely, as the surgeon pushes the down button 810, the surgical controller 102 decreases the speed of the peristaltic pump 130. The speed range controlled by the example non-positional-interface devices may be the entire speed range of the peristaltic pump 130, or may be within predefined speed ranges associated with a selected mode of operation, all as discussed above. Though the example non-positional-interface devices are shown as buttons 808 and 810, any suitable non-positional-interface device may be used (e.g. rocker switch as in FIG. 5D).

The interface devices discussed with respect to FIG. 8 are merely examples, and many variations are possible. For example, the interface device may be a knob devoid of positional markings and that turns about a rotation axis. Turning the knob in a first direction may result in speed of the peristaltic pump increasing, while turning the knob in a second direction opposite the first direction may result in speed of the peristaltic pump decreasing. Further still, the interface device may be a solid state component, such as capacitive touch sensor having a long dimension parallel to the longitudinal central axis of the handle 802. Thus, the surgeon may slide a finger along the touch sensor from the proximal end of the handle 802 toward the distal end 110 to indicate that the speed of the peristaltic pump should increase. And oppositely, the surgeon may slide a finger along the touch sensor from the distal end of the handle 802 toward the proximal end to indicate that the speed of the peristaltic pump 130 should decrease. Knobs devoid of positional markings that indicate setting, capacitive touch sensors, Boolean interaction devices, and others like them, are examples of non-positional-interface devices as previously defined.

Returning to FIG. 6. In FIG. 6 a potentiometer 628 is shown as an example interface with which the processing device 606 may communicate and read position information. Moreover, the example potentiometer 628 is shown electrically coupled to the connector 126. However, in cases in which the resection tool 103 of FIG. 8 is implemented, the interface device may be communicatively coupled to the processing device 606 by way of the connector 142 associated with the electrosurgical generator 608 rather than the connector 126. In yet still further cases, the resection tool 103 may have separate and distinct cables that couple to the surgical controller 102—one cable and connector coupled to the connector 142, and another cable and connector coupled to the connector 126.

Figure 9:
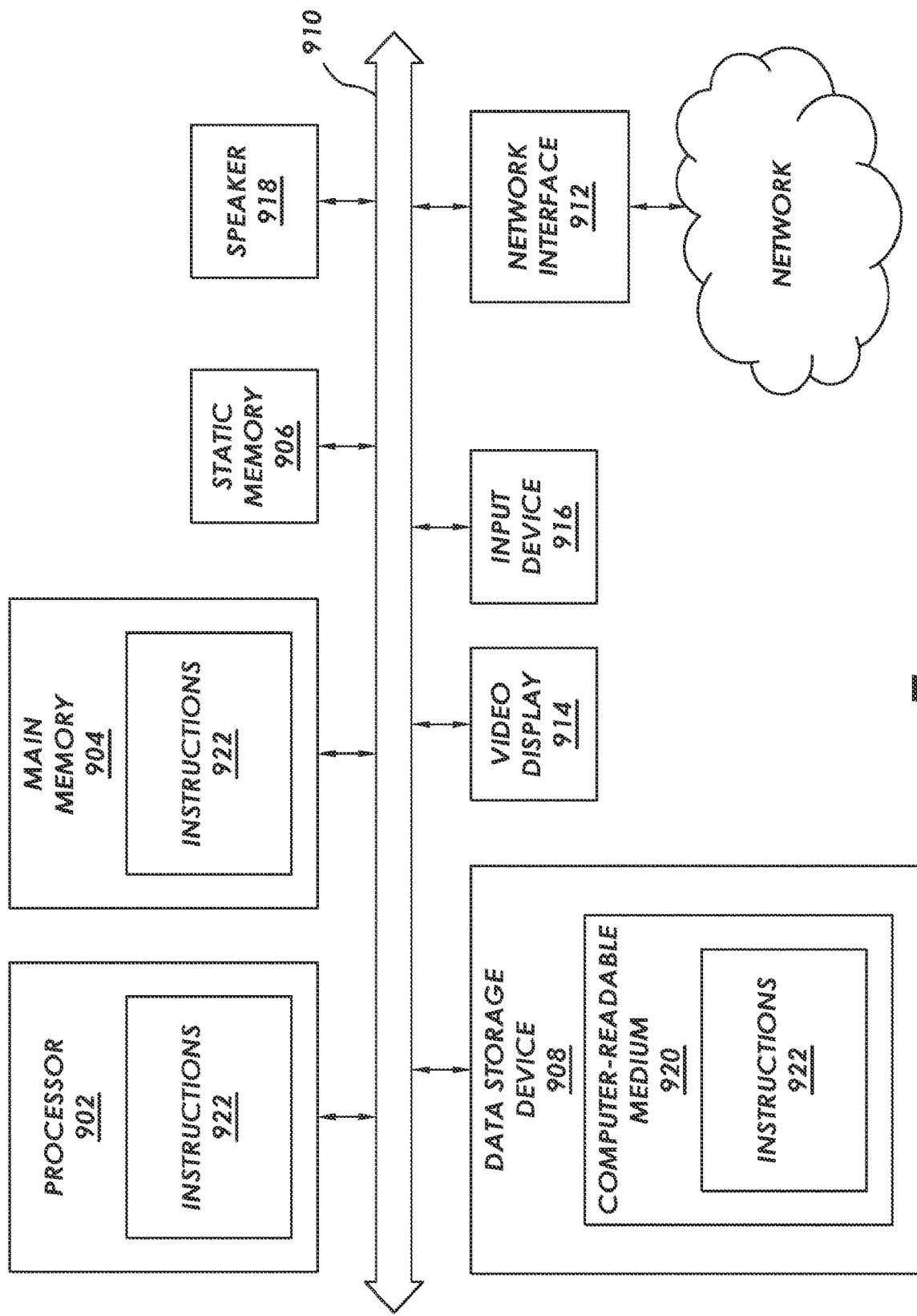
FIG. 9 shows a block diagram of a processing device in accordance with at least some embodiments.

FIG. 9 shows a block diagram of an example processing device 606. In particular, the processing device 606 may be connected (e.g., networked) to other computer systems in a local-area network (LAN), an intranet, and/or an extranet (e.g., device cart network within which the surgical controller 102 is located), or at certain times the Internet (e.g., when not in use in a surgical procedure). The processing device 606 may be a single computer of a group of computers capable of executing a set of instructions (sequential or otherwise) that specify actions to be taken. Further, while only a single processing device 606 is illustrated, the term shall also be taken to include any collection of systems that individually or jointly execute a set (or multiple sets) of instructions to perform any one or more of the methods discussed herein. The processing device 606 includes a processor 902, a main memory 904 (e.g., read-only memory (ROM), flash memory, dynamic random access memory (DRAM) such as synchronous DRAM (SDRAM)), a static memory 906 (e.g., flash memory, static random access memory (SRAM)), and a data storage device 908, which communicate with each other via a bus 910.

Processor 902 represents one or more general-purpose processors such as a microprocessor, central processing unit, or the like. More particularly, the processor 902 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processor 902 may also be one or more special-purpose processing devices such as an application specific integrated circuit (ASIC), a field programmable gate array (FPGA), a digital signal processor (DSP), network processor, or the like. The processor 902 is configured to execute instructions for performing any of the operations and steps discussed herein. Once programmed with specific instructions, the processor 902, and thus the entire processing device 606, becomes a member of a special-purpose device in the form of a surgical controller 102.

The processing device 606 may further include a network interface 912 for communicating with any suitable network (e.g., the device cart network). The processing device 606 also may include the interface device 145 (FIG. 1) in the example form of a video display 914, one or more input devices 916 (e.g., a keyboard, a mouse, digital inputs for reading Boolean values, analog inputs for reading analog values), and one or more speakers 918. In one example, the video display 914 and the input device(s) 916 may be combined into a single component or device (e.g., an LCD touch screen to implement interface device 145).

The data storage device 908 may include a computer-readable storage medium 920 on which the instructions 922 embodying any one or more of the methodologies or functions described herein are stored. The instructions 922 may also reside, completely or at least partially, within the main memory 904 and/or within the processor 902 during execution thereof. As such, the main memory 904 and the processor 902 also constitute computer-readable media. In certain cases, the instructions 922 may further be transmitted or received over a network via the network interface 912.

While the computer-readable storage medium 920 is shown in the illustrative examples to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium that is capable of storing, encoding or carrying a set of instructions for execution by the machine and that cause the machine to perform any one or more of the methodologies of the present disclosure. The term "computer-readable storage medium" shall accordingly be taken to include, but not be limited to, solid-state memories, optical media, and magnetic media.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:

1. A surgical system comprising:
 a resection controller coupled to a motor in a handpiece, and the handpiece coupled to a resection instrument defining a cutting element, and the handpiece comprises an interface device defined on an exterior surface of the handpiece;
 a peristaltic pump controller coupled to a motor of a peristaltic pump, the peristaltic pump coupled to a suction lumen of the resection instrument;
 the surgical system is configured to:
  drive the motor within the handpiece to cause mechanical resection of tissue by the resection instrument;
  aspirate fluid and tissue fragments through the suction lumen of the resection instrument during the mechanical resection of tissue; and
  modulate a speed of the peristaltic pump during the driving and aspirating, wherein the modulation is responsive to the interface device by the surgical system being configured to
   read the interface device, wherein the interface device is a positional-interface device defined on the handpiece, and wherein the reading results in a position associated with the positional-interface device, and
   set the speed of the peristaltic pump based on the position such that the speed of the peristaltic pump is directly and exclusively controlled based on the position.

2. The surgical system of claim 1 wherein the handpiece does not include a valve in an aspiration pathway through the handpiece.

3. The surgical system of claim 1 further comprising:
an electrosurgical controller coupled to an active electrode defined on the resection instrument;
the surgical system is further configured to:
stop the motor of the handpiece at a rotational position such that the cutting element blocks a cutting window defined by the resection instrument; and then
provide electrical energy to the active electrode to cause ablation of tissue proximate to the active electrode.

4. The surgical system of claim 3 wherein the surgical system is further configured to modulate speed of the peristaltic pump during the ablation of tissue, the modulation responsive to the interface device.

5. The surgical system of claim 3 wherein the surgical system is further configured to:
cease the providing of electrical energy to the active electrode; and then
drive the motor within the handpiece, the driving again causes mechanical resection of tissue by the resection instrument; and
aspirate fluid and tissue fragments through the suction lumen at a pump speed selected based on at least one selected from a group comprising: a pump speed of an immediately previous mechanical resection; and a default pump speed for mechanical resection of tissue.

6. A surgical system comprising:
an electrosurgical controller coupled to an active electrode disposed on a distal end of a resection tool;
a peristaltic pump controller comprising a motor and a peristaltic pump, the peristaltic pump coupled to a suction lumen of the resection tool;
wherein the surgical system is configured to:
provide electrical energy to the active electrode to cause ablation of tissue proximate to the active electrode;
draw fluid and tissue fragments through the suction lumen; and
modulate speed of the peristaltic pump during the providing and the drawing, the modulation responsive to an interface device defined on an exterior surface of the resection tool by the surgical system being configured to
read a position of the interface device, wherein the interface device is a positional-interface device defined on the resection tool, and wherein the reading results in a position associated with the positional-interface device, and
set the speed of the peristaltic pump based on the position such that the speed of the peristaltic pump is directly and exclusively controlled based on the position.

7. The surgical system of claim 6 further comprising:
a resection controller coupled to a motor in a handpiece of the resection tool, and the handpiece coupled to a cutting element defined by a resection instrument of the resection tool, the resection instrument coupled to the handpiece;
the surgical system is further configured to:
cease the providing of electrical energy to the active electrode; and then
drive the motor within the handpiece, the driving causes mechanical resection of tissue by the resection instrument; and
aspirate fluid and tissue fragments through the suction lumen of the resection instrument during the mechanical resection of tissue; and
modulate speed of the peristaltic pump during the driving and aspirating, the modulation based on the interface device.

8. The surgical system of claim 7 wherein the handpiece does not include a valve in an aspiration pathway through the handpiece.

9. A surgical system comprising:
an electrosurgical controller coupled to an active electrode disposed on a distal end of a resection tool;
a peristaltic pump controller comprising motor and a peristaltic pump, the peristaltic pump coupled to a suction lumen of the resection tool;
wherein the surgical system is configured to:
provide electrical energy to the active electrode to cause ablation of tissue proximate to the active electrode;
draw fluid and tissue fragments through the suction lumen; and
receive an indication of a selected mode of operation from a plurality of modes of operation, each mode of operation defines a range of pump speeds, and each range of pump speeds less than an entire range of pump speed of the peristaltic pump; and
modulate, within the range of pump speeds of the selected mode of operation, a speed of the peristaltic pump during the providing and the drawing, wherein the modulation is responsive to an interface device defined on an exterior surface of the resection tool by the surgical system being configured to
read a position of the interface device, wherein the interface device is a positional-interface device defined on the resection tool, wherein the reading results in a position, and
set the speed of the peristaltic pump within the range of pump speeds of the selected mode of operation based on the position.

10. The surgical system of claim 9 further comprising:
a resection controller coupled to a motor in a handpiece of the resection tool, and the handpiece coupled to a cutting element defined by a resection instrument of the resection tool, the resection instrument coupled to the handpiece;
the surgical system is further configured to:
cease the providing of electrical energy to the active electrode; and then
drive the motor within the handpiece, the driving causes mechanical resection of tissue by the resection instrument; and
aspirate fluid and tissue fragments through the suction lumen of the resection instrument during the mechanical resection of tissue; and
modulate speed of the peristaltic pump during the driving and aspirating, the modulation based on the interface device.

11. The surgical system of claim 10 wherein the handpiece does not include a valve in an aspiration pathway through the handpiece.

* * * * *